United States Patent
Oben

(10) Patent No.: US 10,905,731 B2
(45) Date of Patent: Feb. 2, 2021

(54) METHODS AND RELATED COMPOSITIONS FOR REDUCING OXIDATIVE STRESS

(71) Applicant: Julius Enyoug Oben, Cameroon (CM)

(72) Inventor: Julius Enyoug Oben, Cameroon (CM)

(*) Notice: Subject to any disclaimer, the term of this patent is extended or adjusted under 35 U.S.C. 154(b) by 137 days.

(21) Appl. No.: 16/426,214

(22) Filed: May 30, 2019

(65) Prior Publication Data
US 2020/0376058 A1 Dec. 3, 2020

(51) Int. Cl.
*A61K 36/00* (2006.01)
*A61K 36/185* (2006.01)

(52) U.S. Cl.
CPC ........ *A61K 36/185* (2013.01); *A61K 2236/33* (2013.01)

(58) Field of Classification Search
CPC ...................................................... A61K 36/00
USPC .......................................................... 424/725
See application file for complete search history.

(56) References Cited

U.S. PATENT DOCUMENTS

2017/0156999 A1* 6/2017 Harris .................. A61K 8/8129

* cited by examiner

*Primary Examiner* — Michael V Meller
(74) *Attorney, Agent, or Firm* — Steve Hassid; Partners Law Group, Inc

(57) ABSTRACT

Oxidative stress is implicated in neurodegenerative diseases such as Alzheimer's disease, and has been extensively studied as a potential target for therapeutic intervention. The present disclosure discloses a method for reducing free radicals in a mammal, the method comprises administering a composition containing an effective amount of *Baillonella toxisperma* extract to a mammal to reduce free radicals in the mammal. Specifically, the present disclosure demonstrates how extracts and flavonoids fractions of *Baillonella toxisperma* provide antioxidant and neuroprotective benefits and prevent oxidative stress in mammals.

18 Claims, 16 Drawing Sheets

METHODS AND RELATED COMPOSITIONS FOR REDUCING OXIDATIVE STRESS

FIELD OF THE DISCLOSURE

The present disclosure relates to methods and related compositions for reducing oxidative stress. Specifically, the one embodiment of the present disclosure reduces the oxidative stress of a mammal by administering the mammal with *Baillonella toxisperma* extract which provides a variety of benefits, including but not limited to reducing free radicals and protecting neurons of a mammal, which in turn allows the prevention and treatment of Alzheimer's and Parkinson's disease.

BACKGROUND

Oxidative stress is the disturbance of the intracellular oxidative status; either by the excessive production of free radicals or by a reduction of the antioxidant defense capacity (Morel et al., 1999). It is implicated in pathologies such as Cardiovascular Disease (CVD), certain cancers, cutaneous aging and neurodegenerative diseases (Morel et al., 1999). Oxidative stress is considered as a major risk factor in the incidence and progression of cognitive decline which usually occurs during normal cerebral aging and plays a critical role in a variety of neurodegenerative processes such as Alzheimer's and Parkinson's diseases (Butterfield et al., 1999). Recent data show that oxidative stress is one of the primordial events involved in the pathogenesis of Alzheimer's disease, where it is implicated in excitotoxicity (a major cause of the death of neurons) (Nunomura et al., 2001).

Many factors such as metabolic disturbances, inflammation, physical agents, cytokines, presence of oxygenated oxidants, oxidative phosphorylation etc. can lead to the production of free radicals (Morel et al., 1999). Free radicals react with oxidisable substrate (i.e. oxygen) and produce carbonyl radicals. The latter have multiple intracellular effects amongst which are glycation of proteins, alteration of DNA structure, generation of products of lipid peroxidation and the modulation of the transcription of numerous genes. The amount of reactive oxygen species is produced in any tissue is directly proportional to its rate of oxygen consumption. The effects of the latter production could accumulate in neurons for years (Nunomura et al., 2001). The brain with its high energy consumption rate is constantly undergoing the oxidation/antioxidation process which makes it highly stress sensitive (Ikonomidou et al., 2011), especially as this process is amplified by intellectual activities such as thinking and reasoning. The antioxidant defense mechanism of the brain traps free radicals and reduces damages which they could cause, but this mechanism cannot always be efficient. This efficiency discrepancy is exacerbated especially when the concentration of reactive oxygen species (ROS) becomes too high, or when the concentration of antioxidants becomes too low. This provokes the destruction of macromolecules such as DNA, lipids, proteins; and eventually the death of the cell by apoptosis and/or necrosis which could lead to many neurological, motor and cognitive inconsistencies and worst still, neurodegenerative disorders of which Alzheimer's (incurable) is the leading disease. (Halliwell and Gutteridge, 1999; Halliwell, 2012). Thus improving cell antioxidant status or reducing its rate of free radical production could be an effective strategy to protect neurons from oxidative damages and therefore prevent the initiation and progression of Alzheimer's disease (Simonian et al., 1996, Mangialasche et al., 2010).

Furthermore, pharmacological and epidemiological studies have shown that nutritional antioxidants can prevent free radical-induced oxidative stress (Behl, 2000) as well as the onset of dementia (Alzheimer's disease) (Orgogozo et al., 1997); in addition, they equally prevent the incidence of cardiovascular diseases (Bearden et al., 2000). Experimentations on animal models and cell cultures have elucidated the neuro-protective properties of a variety of plant extracts as per the incidence of dementia (Defeudis, 2002; Karuppagounder et al., 2009; Aggarwal and Sung, 2009). These beneficial effects were attributed to the anti-oxidative/anti-inflammatory properties of Flavonoids contained in the plant extracts. Ideal neuroprotective therapies should be able to protect neurons against neurotoxins, reactive oxygen species, free radicals, as well as promote the survival of neurons through the regulation of neurotrophic factors (Mandel et al., 2003).

*Baillonella toxisperma* is a plant of the sapotaceae found in Cameroonian forest; used in the treatment of more than fifty diseases/affections (Laird, 2000) in which oxidative stress and inflammatory responses are implicated in the pathogenesis. As such, the present disclosure relates to the study of the effectiveness of extracts of *Baillonella toxisperma* in the elimination of free radicals and protection of neurons from oxidative stress.

SUMMARY OF THE INVENTION

The present disclosure provides plant extracts and related methods that are effective in, among other things, eliminating free radicals and protecting neurons from oxidative stress. Specifically, the present disclosure uses the extract of *Baillonella toxisperma* to reduce the free radicals in the mammal and protect neurons of the mammal from oxidative stress.

In one embodiment of the present disclosure, the present disclosure discloses a method of reducing oxidative stress in a mammal where the method comprises reducing the free radicals of a mammal by administering a composition containing an effective amount of *Baillonella toxisperma* extract to the mammal.

In yet another embodiment of the present disclosure, the effective amount of *Baillonella toxisperma* extract administered is at least 150 mg per day or at least 300 mg per day.

In yet another embodiment of the present disclosure, the *Baillonella toxisperma* extract is obtained from stem bark and of *Baillonella toxisperma*.

In yet another embodiment of the present disclosure, the *Baillonella toxisperma* extract is obtained from flavonoids fractions of *Baillonella toxisperma*.

These and other features, aspects and advantages of the present invention will become better understood with reference to the following drawings, description and claims.

BRIEF DESCRIPTION OF THE DRAWINGS

Figure 3:
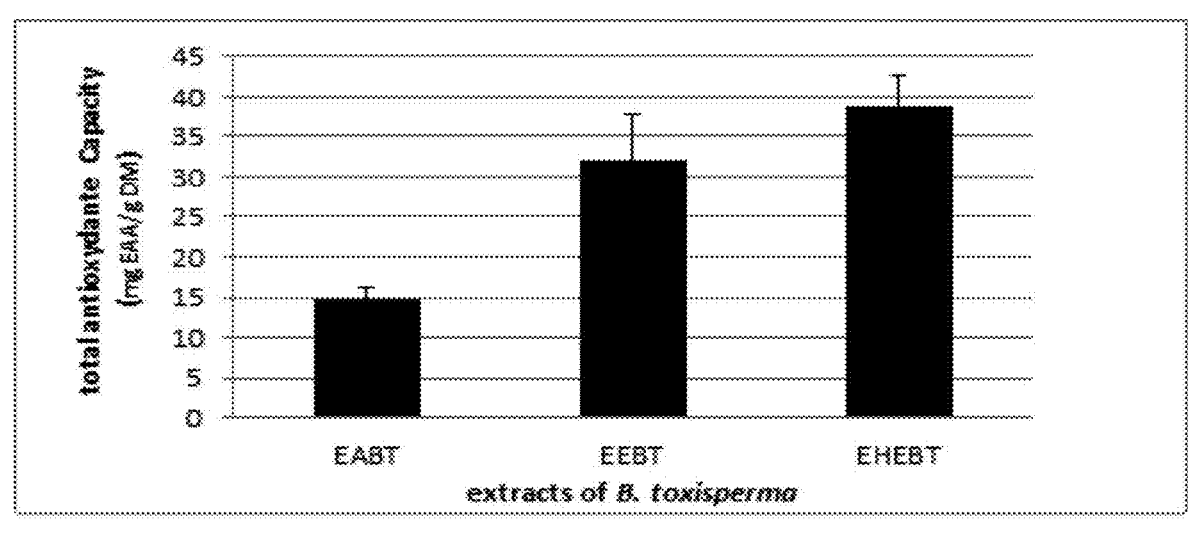

FIG. 3 shows total antioxidant capacity of aqueous, ethanolic and hydroethanolic extracts of *B. toxisperma* in accordance with one embodiment of the present disclosure.

FIG. 8 shows representation of inhibitory concentration 50 values of .OH radical by aqueous, ethanolic and hydroethanolic extracts of *B. toxisperma* and vitamin E

FIG. 11 shows flavonoid content in rough methanolic extract and fractions of *B. toxisperma* in accordance with one embodiment of the present disclosure. EMBBT=rough methanolic extract of *B. toxisperma*; FAEBT=acetyl acetate fraction of *B. toxisperma*; FnBBT=n-butanol fraction of *B. toxisperma*; PARBT=residual aqueous phase of *B. toxisperma*.

DETAILED DESCRIPTION OF THE INVENTION

The following description is not to be taken in a limiting sense, but is made merely for the purpose of illustrating the general principles of the invention. Various inventive features are described below that can each be used independently of one another or in combination with other features.

Broadly, embodiments of the present invention generally relates using extracts and flavonoid fractions obtained from the bark of *Baillonella toxisperma* to protect neurons from oxidative stress and provide benefits as an antioxidant.

In one aspect of the present disclosure, the antioxidant and neuroprotective effects of the bark of *Baillonella toxisperma* on in vivo and in vitro neuro-toxicity models associated to oxidative stress was evaluated. In another aspect of the present disclosure, the effects of extracts and flavonoid fractions of *Baillonella toxisperma* on in vivo and in vitro neuro-toxicity models associated to oxidative stress was evaluated. Specific objectives of the present disclosure further includes evaluating the contents of bioactive compounds in aqueous, ethanolic and hydroethanolic extracts of the bark of *Baillonella toxisperma* as well as their in vitro antioxidant potential; evaluating the neuroprotective effects of the extract with the best in vitro anti-oxidative potential; against neurotoxicity induced by the administration of a single dose of Aluminum in Wistar rats and measurement of some markers of oxidative stress; and extracting flavonoid fractions of the bark of *Baillonella toxisperma* from its methanolic extract and compare the effectiveness of this extract with those of the fractions; in reducing the production of reactive oxygen species induced by hydrogen peroxide in human SK-N-SH neuroblastome cells.

I. Materials and Methods

I.1. Collection of Plant Material, Preparation of Extracts and Evaluation of Contents of Phenolic Compounds I.1.1. Plant Material The bark of the plant, *Baillonella toxisperma* was obtained from Ngoumou in the center region of Cameroon on the 28 Jun. 2012. The obtained bark was sliced into small chips and dried at room temperature until the weight was constant. The chips were then reduced to a fine powder by use of an electric blender. The powder obtained was used for the extraction of Phenols using different solvents.

I.1.2. Preparation of Plant Extracts

Figure 1:
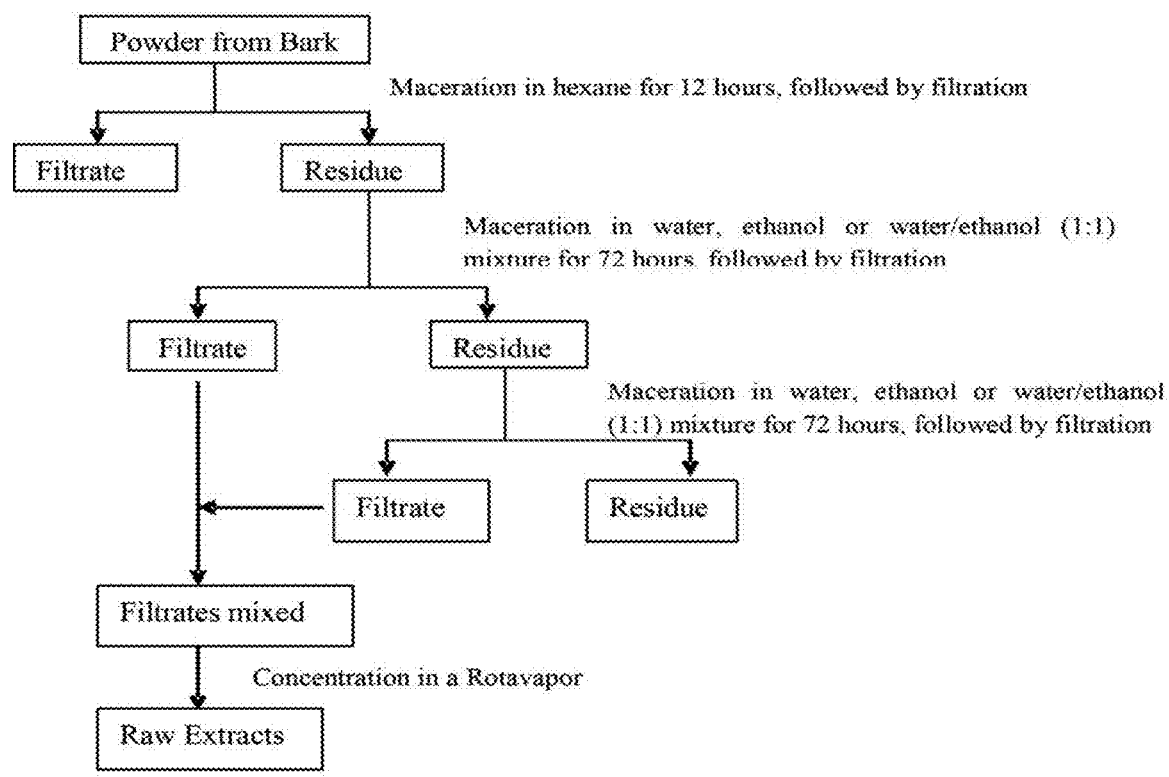
FIG. 1 shows extraction protocol for phenolic compound in *B. toxisperma* in accordance with one embodiment of the present disclosure.

FIG. 1 is an embodiment showing extraction protocol for phenolic compound in *Baillonella toxisperma*. The extraction of phenolic compounds was done using 3 solvents: distilled water, ethanol and a mixture of ethanol/water (1:1) which is commonly called Hydroethanol. 100 g of the powder of *Baillonella toxisperma* bark was first macerated in 1000 ml of hexane for 12 hours to eliminate lipids. 50 g of the residue was later macerated in 500 ml of each of the 3 solvents mentioned earlier for 72 hours at room temperature (2 extractions each). Each mixture was filtered using Whatman No 1 paper. The filtrates were then concentrated in a Rotavapor at 50° C. and the raw extracts obtained were then collected into small tubes and stored at 4° C. and away from sunlight. The content of phytochemical compounds and antioxidant potential was later evaluated.

I.1.2. Determination of the Content of Total Phenols (McDonalds, 2001)

Principle:

This method uses Folin-Ciocalteu's reagent and is based on the reduction of a yellow colored Molybdotungstane complex in alkaline medium by phenolic compounds to give a reaction product which is blue in color Protocol:

100 μL of each extract (1 mg/mL prepared in methanol) or methanol (blank) was added to test tubes containing 1 mL of Folin-Ciocalteu's reagent (annexe 3a) (1:10 dilution using distilled water) and 0.8 mL of sodium carbonate ($Na_2CO_3$, 1 M) solution. The test tubes were then agitated for 15 minutes. The absorbance was read at a wavelength of 765 nm using the blank as titer. Polyphenol content was expressed as equivalent milligram (mg) of Gallic acid per gram (g) of dry matter (mg EGA/g DM); and their values obtained by comparing values with those from the standard curve that was drawn after preparing concentrations of Gallic acid under similar conditions. All samples were analyzed in triplicates.

I.1.3 Evaluation of Flavonoids Content (Bahorun et al., 1996)

Principle:

Flavonoids present in a sample react with aluminum trichloride and potassium acetate to give a pink-like colored solution.

Protocol:

To 1 mL of test sample prepared in methanol (mg/mL) were added 1 mL of a solution aluminum trichloride dissolved in methanol (2% w/v) and 1 mL of potassium acetate (1M). After incubating for 10 minutes, the absorbance was read at 430 nm against a blank. The blank was prepared in a similar manner but without the test sample. The values of Flavonoids content were expressed as equivalent milligrams of Quercetine per gram of dry matter (mg Eq/g DM); and determined by comparing optical densities read through photo-spectroscopy with those on a standard Quercetine curve. This Quercetine curve was established using a range of Quercetine concentration prepared under similar conditions. All samples were prepared in triplicates.

I.1.4 Evaluation of Proanthocyanes Content (Sun et al. 1998)

Principle:

In the presence of a solution of concentrated HCl, proanthocyanes (condensed tannins) contained in a sample are converted to anthocyanidines through an auto-oxidation of carbonations formed by cleaving inter-Flavonoid bonds. The anthocyanidins formed react with vanillin dissolved in methanol to form a complex whose absorbance is read at 530 nm.

Protocol:

To 3 mL of vanillin dissolved in methanol (4% w/v) were added 1.5 mL of HCl (1N) and 0.5 mL of extract (1 mg/mL prepared in methanol). The mixture was agitated then allowed to stand for 15 minutes at room temperature. The absorbance was read at 530 nm against a blank. The values of proanthocyane content were expressed in equivalent milligrams of Cyanidine acid per gram of dry matter (mg Eq AC/g DM); and determined by comparing optical densities read through photo-spectroscopy with those on a standard Cyanidic acid curve. This Cyanidic acid curve was established using a range of concentration prepared under similar conditions. All samples were prepared in triplicates.

I.2. Evaluation of the In Vitro Antioxidant Capacity of Extracts of *Baillonella toxisperma*

I.2.1 Total Antioxidant Capacity (TAC) (Prieto et al., 1999).

Principle:

This technique is based on the reduction of molybdenum (VI) in molybdate ion ($MoO_4^2$) to molybdenum (V) in $MoO^{2+}$ ion in the presence of extracts to form a green phosphate complex in acid medium.

Protocol:

0.3 mL of each extract prepared in methanol was mixed with 3 mL of the reagent solution (equal volumes of 0.6 M sulfuric acid, 0.28 mM sodium phosphate and 4 mM ammonium molybdate) in test tubes. The tubes were corked and incubated at 95° for 90 minutes. After cooling the absorbance was read at 695 nm against a blank which was composed of 3 mL of reagent solution and 0.3 mL of methanol incubated in similar conditions as test samples. The total anti-oxidant capacity was expressed as the equivalent mg of ascorbic acid per gram of dry matter (mg EAA/g DM). Values were obtained by comparing against a standard ascorbic acid curve drawn after preparing a range of ascorbic acid concentrations under similar conditions. All test samples were analyzed in triplicates.

I.2.2 Ability to Trap the 2,2-Diphenyle-1-Picrylhydrazyle (DPPH.) Radical (Sanchez-Moreno et al., 1998)

Principle:

This method is based on the reduction of an alcoholic solution of the stable form of the DPPH. radical in the presence of an antioxidant donor of hydrogen (AH), which leads to the formation of a non-radical form DPPH-H. This reduction causes a color change from violet to yellow which could be studied at 517 nm. The faster the color change occurs, the more the donor is considered as a strong antioxidant.

Protocol:

50 µL of different concentrations of each extract was added to 1.950 mL of freshly prepared methanolic DPPH. (0.025 g/L). After incubation for 30 minutes in the dark and at room temperature, the absorbance was read at 517 nm. Methanol was used as control and ascorbic acid was used as standard. The ability to trap DPPH. was expressed in percentage inhibition as calculated using the following equation:

$$\text{Pourcentage inhibition} = \frac{\text{Absorbance(control)} - \text{Absorbance(test)}}{\text{Absorbance(control)}} \times 100$$

The inhibitory concentrations 50 ($IC_{50}$) were later determined by extrapolating after drawing curves of percentage inhibition against concentration. All samples were analyzed in triplicates.

I.2.3 Ability to Trap the Hydroxyl (.OH) RADICAL (Halliwell et al., 1987)

Principle:

The in vivo capacity of plant extracts to trap the hydroxyl radical is based on the Fenton reaction, by measuring the production of .OH radical and its effect on the oxidation and degradation bio-molecules such as deoxyribose in DNA. The system in this technique involves an auto-oxidation of the $Fe^{2+}$-EDTA complex in an aqueous medium to form the superoxide ($O_2^-$.) anion which is rapidly dismutated into $H_2O_2$ at a pH of 7.4. The latter then reacts with $Fe^{2+}$ form .OH radicals in the presence of ascorbic acid which acts as catalyst (Fenton reaction). The degradation of deoxyribose by .OH gives off some products estimated in malondialdehyde (MDA), from a pink chromogen during heating with thiobarbituric acid. The presences of anti-radicals protect and reduce the production of MDA. The role of ascorbic acid is to reduce $Fe^{3+}$ to $Fe^{2+}$ causing the Fenton reaction to occur ($Fe^{3+}$-EDTA+ascorbate $Fe^{2+}$-EDTA+ascorbate oxyde).

Protocol:

The reaction mixture contained the following reagents: 0.4 mL of phosphate buffer (50 mmol/L, pH=7.4), 0.1 mL of different concentrations of the extract, 0.1 mL of EDTA (1.04 mmol/L), 0.1 mL of $FeCl_3$ (1 mmol/L) and 0.1 mL 2-deoxyribose (60 mmol/L). the reaction was initiated by adding 0.1 mL of ascorbic acid (2 mmol/L) and 0.1 mL of $H_2O_2$ (10 mmol/L). after incubating for 1 hour at 37° C., 1 mL of TBA (10 g/L) were added into the reaction medium followed by 1 mL of HCl (25% v/v). The mixtures were placed in a water bath at 100° C. for 15 minutes then cooled in fresh water. The absorbance was then read at 532 nm. The capacity of extracts to trap the hydroxyl radical was expressed as percentage inhibition of the oxidation of 2-deoxyribose based on the following formula:

$$\text{Pourcentage inhibition (\%)} = \frac{A0 - (A1 - A2)}{A0} \times 100$$

Where $A_0$ represents the absorbance of the control without extract, $A_1$: the absorbance after adding extract and deoxyribose, $A_2$: the absorbance of the extract without deoxyribose. Vitamin E was used as standard and the experiment was performed in triplicates. The inhibitory concentrations 50 ($IC_{50}$) were determined by extrapolating after drawing percentage inhibition curves.

I.2.3 Inhibitory Activity of Lipid Peroxide in Nitro (Prasanth et al., 2000)

Principle:

Lipid peroxidation refers to the oxidative degradation of lipids which provoke a continuous increase in the permeability of cell membranes, inducing an irreversible alteration of the functional properties of the cell which could eventually lead to cytolysis. It is a radical chain reaction in which a free radical cleaves a hydrogen atom from membrane lipids in order to form a conjugated diene radical, which is oxidized to a peroxyl that in turn generates other radical reactions leading to the formation of terminal products such as MDA. Iron can stimulate lipid peroxidation either by Fenton reaction or by acceleration of peroxidation through the decomposition of lipid hydroperoxides into peroxyl or alkoxyl radicals; themselves capable of cleaving a hydrogen and perpetuating lipid peroxidation. The MDA from this reaction reacts with TBA to give pink colored chromophores which absorb at 532 nm.

Protocol:

Male Wistar rats were randomly chosen and kept for overnight fasting. They were later sacrificed by decapitation after anesthesia by ether. Their brains were then rapidly removed and rinsed in 0.15 M KCl. 10% homogenates were then prepared in KCl and centrifuged at 1500 revs/minute 15 minutes and filtered to obtain a clear solution which was then used as a source of poly unsaturated fatty acids for eventual evaluation of the degree of lipid peroxidation.

The lipid peroxidation test was conducted as follows: 300 μL of plant extract at different concentrations and distilled water (control) were added to 500 μL of each homogenate. The mixture was then incubated with KCl (0.15 M, 100 μL); and lipid peroxidation was induced by adding 100 μL of a solution of $FeSO_4$ (15 mM). The reaction mixture was later incubated 37° C. for 30 minutes. Equal volumes (1:1) (1 mL) of TBA (1% p/v) and HCl (10% v/v) were added to the solution followed by ascorbic acid (6 mM, 1 mL). The final mixture was heated at 80° C. for 20 minutes in a water bath and centrifuged. The absorbance was read at 532 nm. Vitamin E was used as standard and the experiments conducted in triplicates. The $IC_{50}$ were determined by extrapolating after drawing curves of lipid peroxidation percentage inhibition against the concentrations of plant extracts.

$$\text{pourcentage inhibition(\%)} = \frac{\text{Absorbance(control)} - \text{Absorbance}}{\text{Absorbance(control)}} \times 100$$

I.3. Evaluation of Neuro-Protective Effects of the Hydro-Ethanolic Extract of *B. toxisperma* Against Aluminum Chloride Induced Neurotoxicity (Animal Model of Neurotoxicity)

Twenty albinos Wistar rats weighing between 230-250 g were used for this experiment in which the treatment lasted 3 days. The experimentation was conducted in the animal house of the Laboratory of Nutrition and Nutritional Biochemistry of the department of Biochemistry (Faculty of Science, University of Yaounde I). Animals were fed with standard feed and drinking water ad libitum.

I.3.1. Experimentation Protocol

Rats were divided into 5 groups of 4 rats each. A unique dose of 32.5 mg/kg BW of aluminum trichloride ($AlCl_3$) was administered by intra peritoneal (i.p) route. 24 hours later, different doses of plant extract and vitamin E (reference) were administered by oral route, using a gastro-oesophagian probe once a day for 3 days.

TABLE 1 distribution of animals per test group of Aluminum induced neuro-toxicity

| Groups | Treatment |
| --- | --- |
| Group 1 (NC) | NaCl 0.9% |
| Group 2 (PC) | 32.5 mg/kg $AlCl_3$ + NaCl 0.9% |
| Group 3 ($BT_{150}$) | 32.5 mg/kg $AlCl_3$ + 150 mg/kg. BW/day de *B. toxisperma* |
| Group 4 ($BT_{300}$) | 32.5 mg/kg $AlCl_3$ + 300 mg/kg. BW/day de *B. toxisperma* |
| Group 5 ($VE_{100}$) | 32.5 mg/kg $AlCl_3$ + 100 mg/kg. BW/day of Vit E |

Where NC: Negative Control, PC: Positive Control, $BT_{150}$: extract of *Baillonella toxisperma* 150 mg/kg BW, $BT_{300}$: extract of *Baillonella toxisperma* 300 mg/kg BW, $VE_{100}$: vitamin E 100 mg/kg de PC, BW: Body Weight.

24 hours after the last administration, animals were sacrificed under mild anesthesia in Ether vapor following a 12 hours fasting. The rats' bloods were collected in EDTA tubes. Cervical dislocations were performed immediately after blood collections, to remove the brains which were then rinsed in physiologic solution (0.9% NaCl) and weighed. Plasmas were extracted from the bloods collected and the brains were used to prepare 10% homogenates which served for biochemical analysis.

I.3.2. Preparation of Plasmas and Homogenates

The blood in EDTA tubes were allowed to stand at room temperature, then centrifuged for 10 minutes at 900 revs/minute, the resulting liquid phase (plasma) was then collected into Eppendorf tubes and stored at −20° C.

Homogenates of the brains were prepared at 10% as described earlier except for the fact that KCl was replaced by NaCl 0.9% (w/v) and stored at −20° C.

I.3.3. Biochemical Analysis

I.3.3.1. Titration of Malondialdehyde (MDA) (Yagi, (1976)

Principle:

carbonyl compounds such as malondialdehyde react with thiobarbituric acid (TBA) to give pink colored chromophores which absorb at 532 nm.

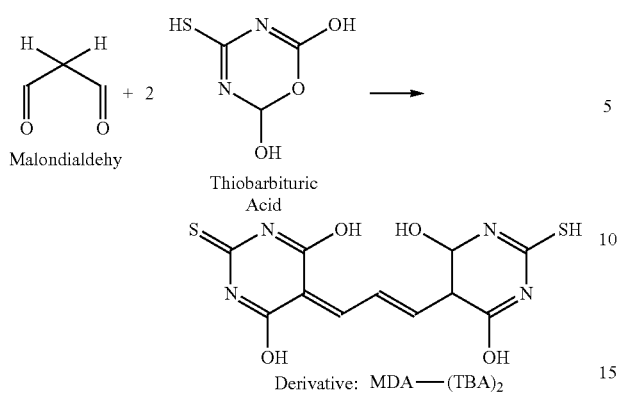

Malondialdehy + 2 Thiobarbituric Acid

Derivative: MDA—(TBA)₂

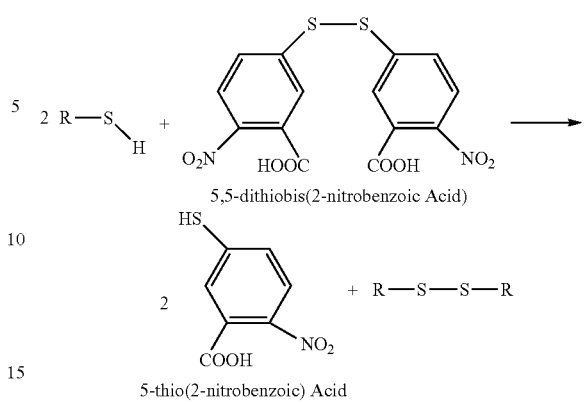

5,5-dithiobis(2-nitrobenzoic Acid)

5-thio(2-nitrobenzoic) Acid

R = variable protein Radical

Protocol:

100 µL of homogenate and 400 µL of TBA reagent (annex 3b) were introduced into glass test tubes (blank and assay) which were tightly corked. The mixture was the heated in a water bath at 100° C. for 15 minutes then allowed to cool in a cold water bath for 30 minutes. The tubes were later opened for any gas to evaporate before centrifugation for 5 minutes at 1500 revs/minute and the absorbance of the liquid phase was read at 532 nm against a blank which contained 400 µL of reagent solution and 100 µL of NaCl 0.9% incubated in similar conditions. The concentration of MDA was determined using it molar extinction coefficient ($\varepsilon = 1.53 \times 10^5$ $M^{-1} \cdot cm^{-1}$) and the following formula.

$$\text{Concentration } MDA\left(\mu\frac{\text{mol}}{L}\right) = \frac{DO}{\varepsilon l}$$

I.3.3.2. Markers of Non-Enzymatic and Enzymatic Antioxidant Systems

I.3.3.2.1. Titration of Totales Proteins by Biuret's Method (Gornall et al., 1949)

Principle:

In the presence of an alkaline tartrate solution, a blue complex is formed with copper salt when a protein solution is added. The latter reacts with tartrate to form an insoluble blue coordinate complex which absorbs at 540 nm. The color intensity is proportional to the protein content of the sample.

Protocol:

The assay tubes contained 100 µL of homogenate or plasma or ovalbumin (caliber) and 3 mL of Biuret's reagent (annex 3c). After 30 minutes of incubation in the dark and at room temperature. The optical densities were read at 540 nm against a blank which contained 3 mL of reagent solution and 100 µL of NaCl 0.9% incubated under similar conditions. The total protein concentration was determined from the following equation:

$$\text{protein Concentration} = \frac{\text{Absorbance of assay}}{\text{Absorbance of caliber}} \times \text{concentration of caliber}$$

I.3.3.2.2. Titration of Protein Thiols (Ellman, 1959)

Principle:

This method is based on a measure of thiol groups by following up the concentration of TNB (5-thio (2-nitro-benzoic) acid) which is yellow in color, and formed when DTNB-(5,5-dithiobis (2-nitrobenzoïque) acid) is reduced.

Protocol:

100 µL of homogenate and 900 µL of Ellman's reagent (annex 3d) were added into the assay tubes, homogenized and incubated at room temperature for 30 minutes before reading the optical densities at 412 nm against a blank which contained 900 µL the reagent solution and 100 µL of NaCl 0.9% incubated under similar conditions as the assay. The concentration of thiol groups (SH) were determined using the molar extinction coefficient of DTNB ($F = 1.36 \times 10^4$ $M^{-1} \cdot cm^{-1}$). Results were expressed as mol/g of total proteins.

I.3.3.2.3. Evaluation of Catalase Activity (Sinha 1972)

Principle:

This method is based on the fact that the catalase present in hemolysates or homogenates reduces hydrogen peroxide ($H_2O_2$) to water ($H_2O$) and oxygen ($O_2$). The $H_2O_2$ that wasn't reduced by catalase then bonds to potassium dichromate to form an unstable blue green precipitate. The latter is then decomposed by heat to form a green complex which absorbs at a wavelength of 570 nm. Catalase activity is proportional to the optical density and is determined by use of a calibration curve.

TABLE 2

Preparation of tubes for catalase calibration curve

| No | 1 | 2 | 3 | 4 | 5 |
|---|---|---|---|---|---|
| $H_2O_2$ (µL) 50 mM | 0 | 20 | 40 | 80 | 160 |
| $H_2O$ (µL) | 1000 | 980 | 960 | 920 | 940 |
| $H_2O_2$ (mM) | 0 | 1 | 2 | 4 | 8 |
| solution de Dichromate/acide-acétique (mL) | 2 | 2 | 2 | 2 | 2 |

Protocol:

50 µL of homogenate and 750 µL of phosphate buffer (0.01 M; pH 7.0) were successively added into test tubes followed by 200 µL of hydrogen peroxide (200 mM). A stopwatch was activated after adding 2 mL of a solution of dichromate/acetic acid (1:3 v/v mixtures of potassium dichromate 5% and concentrated acetic acid). The reaction was stopped after 60 seconds. Control tubes were prepared simultaneously and all tubes were heated to 100° C. for 10 minutes. After cooling, the optical densities were read at 620 nm against the blank (50 µL of NaCl 0.9% treated under similar conditions).

Catalase activity was expressed in micromoles of $H_2O_2$ consumed/min/mg of protein.

I.3.3.3. Titration of Parameters of Hepatic and Renal Toxicity

I.3.3.3.1. Evaluation of the Activities of the Oxaloglutamate (GOT) and Glutamo-Pyruvate (GPT) Transaminases (Reitman et Franckel, 1957) (hepatic toxicity)

Principle:

GOT (EC 2.6.1.1) and GPT (EC 2.6.1.2) catalyze the following reactions:

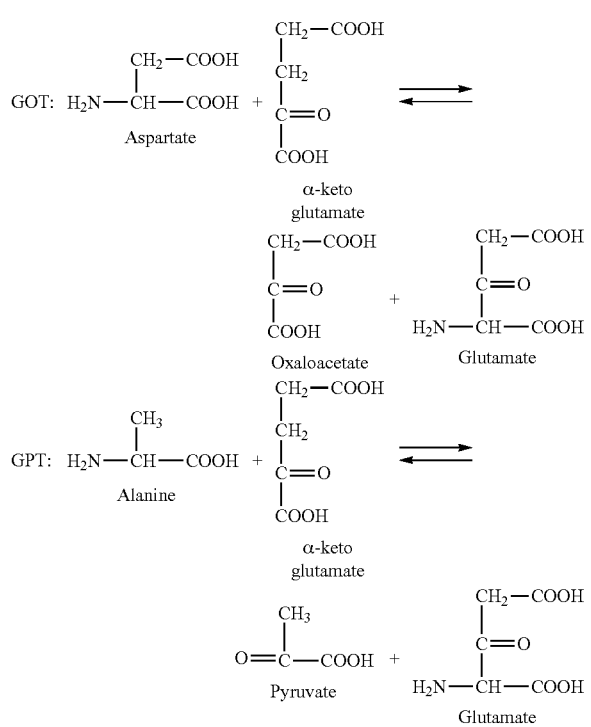

The Pyruvate and Oxaloacetate formed were titrated through 2,4 dinitrophenyl hydrazine which is their derivative and has a maximum absorption at 505 nm Protocol: Evaluation De L'Activite De L'Asat (GOT):

100 µL of substrate solution (annex 3e) were put into tubes, pre-incubated at 37° C. for 5 minutes then 0.02 mL of plasma was added. After homogenization, tubes were then incubated at 37° C. for 1 hr and 0.1 mL of the coloration reagent (annex 3e) was then added. Tubes were then allowed to stand at room temperature for 20 minutes; the reaction was stopped by adding 1 mL of NaOH. Optical densities were read at 505 nm against a blank (made up of 100 µL of substrate solution and 0.02 mL of NaCl 0.9%) titrated under similar conditions. The optical densities obtained were used to determine the activity of ASAT from the calibration curve; which itself was drawn using the data in table 3 below.

TABLE 3

Preparation of tubes for calibrating the activity of transaminases

| Tubes | 1 | 2 | 3 | 4 | 5 | 6 |
|---|---|---|---|---|---|---|
| Distilled water (mL) | 0.1 | 0.1 | 0.1 | 0.1 | 0.1 | 0.1 |
| Substrate GOT (mL) | 0.1 | 0.09 | 0.08 | 0.07 | 0.06 | 0.05 |
| Sodium Pyruvate (mL) | 0 | 0.01 | 0.02 | 0.03 | 0.04 | 0.05 |
| DNPH | 0.1 | 0.1 | 0.1 | 0.1 | 0.1 | 0.1 |

TABLE 3-continued

Preparation of tubes for calibrating the activity of transaminases

| Tubes | 1 | 2 | 3 | 4 | 5 | 6 |
|---|---|---|---|---|---|---|
| Incubation 20 minutes room temperature | | | | | | |
| NaOH (mL) | 1 | 1 | 1 | 1 | 1 | 1 |
| Allowed at room temperature for 5 minutes then read OD at 505 nm against blank | | | | | | |
| Corresponding Activities | | | | | | |
| GOT (units of ASAT/mL) | 00 | 22 | 55 | 95 | 150 | 215 |
| GPT (units of ALAT/mL) | 00 | 25 | 50 | 83 | 126 | 200 |

Evaluation of the Activity of ALAT (GPT) (Reitman and Franckel, 1957):

For ALAT the protocol is same as that described earlier, except for the fact that the incubation time was 30 minutes.

I.3.3.3.2. Titration of Creatinine (Renal Toxicity) (Bartels et al., 1972)

Principle:

In alkaline medium, creatinine forms an orange yellow complex with picric acid. The intensity of the coloration is proportional to the concentration of creatinine in the medium.

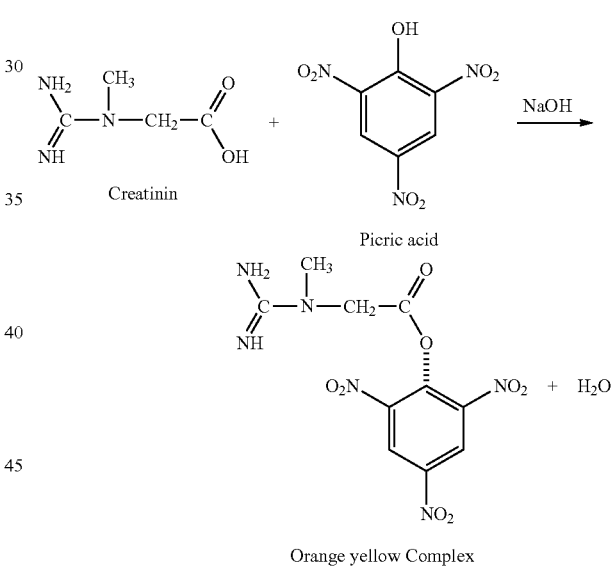

Protocol:

1 mL of working solution (annex 3f) was placed into test tubes and 0.1 mL of plasma and caliber added respectively to assay and blank tubes. Tubes were agitated and their optical densities read 520 nm against a blank; within the 20 seconds that followed the stabilization of the mixture. The blank contained 0.1 mL of NaCl 0.9% and 1 mL of the working solution prepared under similar conditions. The concentration of creatinine was determined from the following equation:

$$\text{creatinin Concentration (mg/dL)} = \frac{\text{Absorbance (assay)}}{\text{Absorbance (caliber)}} \times \text{Concentration (caliber)}$$

I.3.4. Statistical Analysis

SPSS (Statistical Package for Social Science) Version 10.1 for Windows and CytoSoft 5.3 software was used to analyze the result. Variations amongst groups were analyzed by one factor ANOVA (Analysis of variance) tests. Tamhane and Duncan's test was used for post hoc comparison of aluminum induced neuro-toxicity values in rats. Kolmogorov-Smirnov test was used to compare independent groups. Results having $p<0.05$ were considered as significant. Results were expressed as the mean standard deviation.

I.4. Study of Antioxidants in the Rough Methanolic Extract and Flavonoid Fractions of *B. toxisperma*

I.4.1. Extractions of Flavonoid Fractions (Bekkara et al., 1998 modified)

Figure 2:
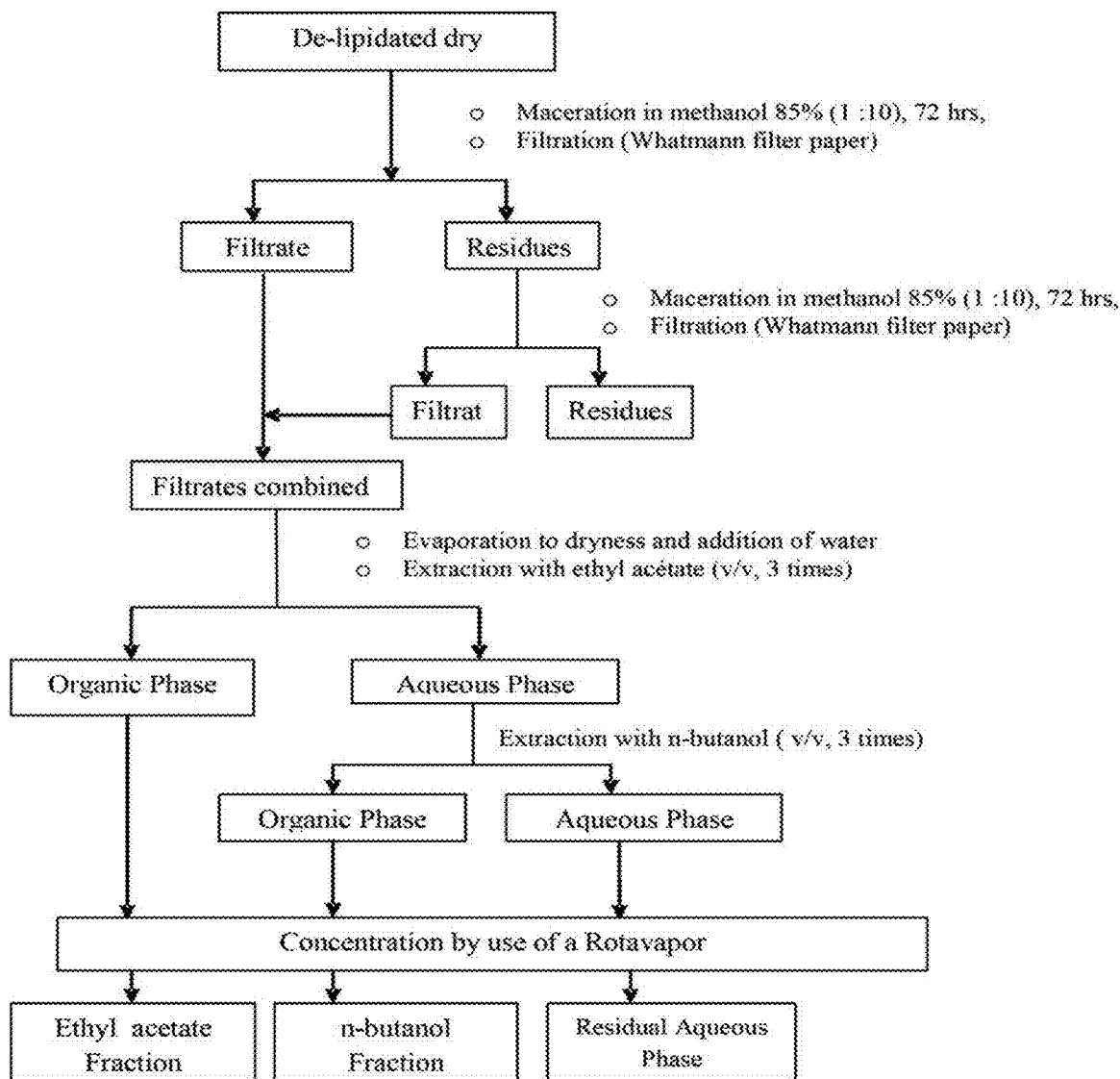
FIG. 2 shows protocol for fractionation of flavonoids in *B. toxisperma* in accordance with one embodiment of the present disclosure.
Figure 4:
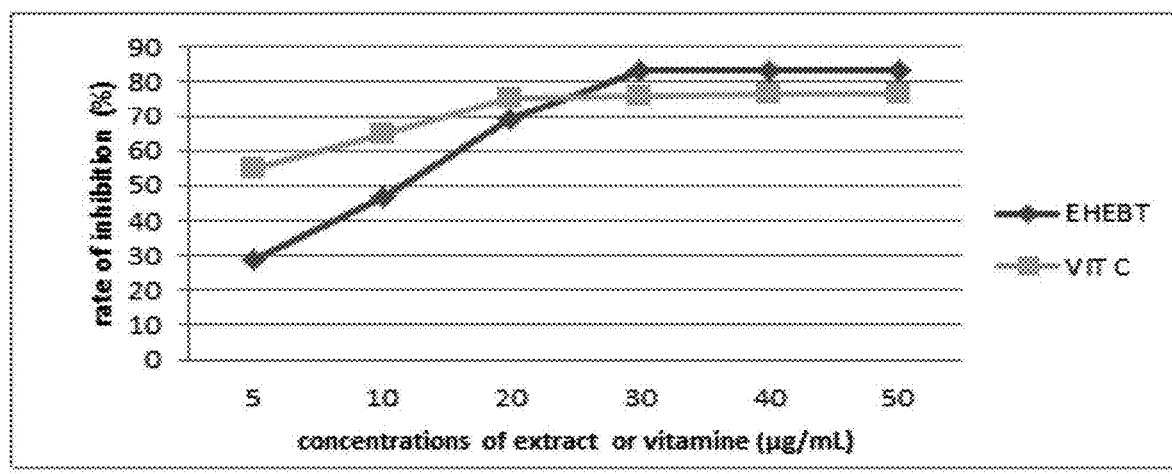
FIG. 4 shows variation curves of percentage inhibition of DPPH. radical by different concentrations of hydroethanolic extract of *B. toxisperma* and vitamin C (standard) in accordance with one embodiment of the present disclosure.
Figure 5:
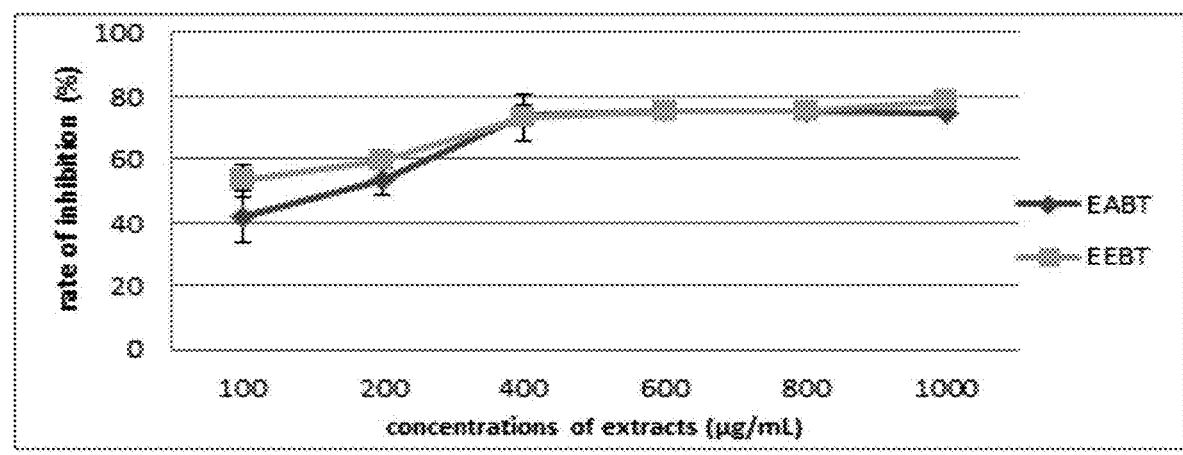
FIG. 5 shows variation curves of percentage inhibition of DPPH. radical by different concentrations of aqueous and ethanolic extract of *B. toxisperma* in accordance with one embodiment of the present disclosure.

Principle:

It is based on the extent of dissolution of flavonoids in organic solvents (FIG. 2). This method involves two major steps: the first is extraction using methanol to dissolve Flavonoids and the second is extraction done using ethyl acetate (extraction of monoglycosides) and n-butanol (to dissolve di and triglycosides).

Protocol:

FIG. 2 shows Protocol for fractionation of flavonoids in *B. toxisperma* in accordance with one embodiment of the present disclosure. The grind and delipidated (using hexane) plant material was subjected to another extraction by macerating in methanol (85%) for 72 hours (done twice). The mixture was filtered afterwards using Whatmann No 1 filter paper. The filtrates were later desiccated almost to dryness by use of a rotavapor at 40° C. The residue was then dissolved in distilled water to separate mono and di and triglycosides, and the aqueous phase was mixed with ethyl acetate (v:v) (3 extractions) to obtain an organic phase containing aglycone Flavonoids and monoglycosides. The aqueous phase was mixed with n-butanol (v:v) (3 extractions) to precipitate Flavonoids, di and triglycosides. The final aqueous phase contains mostly very polar glycosyl flavonoids. These confrontations were done in decantation tubes and each time, the aqueous phase and the solvent were agitated vigorously then allowed to rest for 30 minutes in order to ensure effective separation before collecting the different phases into different containers.

I.4.2. Evaluation Flavonoids Content in Rough Extract Fractions

Flavonoids content was estimated following the method of Bahorun et al. (1996) as described earlier, except for the fact that values this time were expressed in microgram (g) equivalent (−)-epigallocatechine-3-gallate per gram of dry matter (g EGCG)/g DM).

I.4.3. Evaluation of DPPH. Anti-Radical Activity of Rough Extract Fractions

This activity was evaluated using the protocol of Sanchez-Moreno et al. (1998) as described earlier.

I.4.4. Evaluation of the Antioxidant Activity of Rough Extract Fractions

These experimentations were conducted in the Neurophamacology laboratory of the Armand-Frappier institute, National institute for scientific research, Quebec, Canada.

I.4.4.1. Cellular Model

Cells obtained from a linage of human SK-N-SH neuroblastoma through triple sub-cloning (Biedler et al., 1978). A neuroblastoma is a tumor in the neural crest of young children. These cells have a neuroblastic morphology with noradrenergic properties, neuron-specific enzyme activity, possible internalization of norepinephrine, neuron-specific proteins such as neurofilaments, neuron-specific activities such as the conversion of glutamate into the neurotransmitter gamma amino butiryl acid (GABA).

The cells were cultured in a RPMI 1640 (Roswell Park Memorial Institute 1640) medium, buffered with sodium bicarbonate, supplemented with 2 mM glutamine and fetal bovine serum (10%). An antifungal and antibiotic mixture (anti-fungi 2.5 mg\mL; penicillin 1.25 U/mL and streptomycin 0.00125 U/mL) was used to prevent contamination by microorganisms. Cells were cultured in 75 $cm^2$ culture flasks containing 15 mL culture medium and antibiotics. The flasks containing cell suspension were later placed in an incubator (temperature 37° C.) under an atmosphere of 5% $CO_2$. The medium was renewed once every week. At the point of confluence, the cells were re-inseminated following the method below:

The medium was eliminated by aspiration and the carpet of cells rinsed twice with 7 mL of sterile phosphate buffer (PBS: Phosphate buffer saline without $Ca^{+2}$ or $Mg^{+2}$), then 3 mL of trypsin (2.5%) without EDTA were added to the flasks.

The cells were incubated for 5 minutes at 37° C. Once cells were dissociated, enzyme action was stopped by adding 7 mL of RPMI medium. (for cell amplification: 1 mL of this cell suspension was cultured in 15 mL of culture medium with antibiotics as described earlier on).

Cell counting was done on a Neubauer cell, using Trypan blue, a colorant which reflects modifications in cell membrane permeability; with the aid of an optic microscope (objective: ×10). The volume of cell suspension was readjusted when necessary by adding a given amount of culture medium to achieve desired concentrations.

Evaluation of Cell Growth: Bleu Trypan Test

Trypan blue is a colorant which is capable of specifically coloring the nucleus of dead cells; it does not color living cells because it cannot penetrate a living plasma membrane. At confluence, cells were trypsinated and placed once again in suspension in 6 mL of culture medium. After homogenization, 100 μL of the Suspension was mixed with 100 μL of 0.4% trypan blue solution. A drop of the mixture was later deposited on a counting cell (Neubauer cell) and the number of dead and living cells counted with the aid of an optic microscope.

I.4.4.2. MTT Based Cytotoxicity Test (Hansen et al., 1989) of the Rough Extract of Flavonoid Fractions on SK-N-SH Cells Principle:

It is a colorimetric technique of measuring the viability of cells. The cell viability is evaluated by measuring the activity of the mitochondrial enzyme, succinate dehydrogenase (SD) of living cells. This enzyme catalyzes the dehydrogenation of succinic acid within the Krebs cycle, to form fumeric acid. This method is based on the ability of living cells to reduce a yellow colored tetrazolium salt (3-[4,5-Dimethylthiazol-2-yl]-2,5-diphenyltetrazolium bromide) by use of the enzyme SD to form a blue colored formazan salt; this enables the colorimetric follow up of cell respiration. This technique permits an evaluation of the effect of a molecule (with respect to concentration or time of incubation) on the survival of a cultured cell.

Protocol:

The test was conducted on sterile microplates of 96 wells (20 000 cells/well). The cells (20 000) were incubated in 100 μL of culture medium. The control was made up of a column of wells containing 100 μL of culture medium only, and another column containing cells in culture medium, but which were not subject to any treatment. In the test wells, after 24 hours of growth, the cells were subjected to treatment with different concentrations of fractions of *B. toxisperma*; so as to evaluate their effect on the viability of cells. After treatment 10 μL of the tetrazolium salt (5 mg in PBS) were added to each well (ie ⅟₁₀ of the initial volume of culture, making a final concentration of 0.5 mg/mL), and the cells were incubated at 37° C. for 2 hours. After incubation, the medium was aspired with care to avoid aspiration of the blue formazan crystals that were formed. DMSO was later added in order to dissolve the crystals in each well and the microplate was agitated (for about 5 minutes) until the color in each well was homogenous. The optical density was read at 570 nm using a spectrophotometer that reads microplates directly. The optical densities obtained are directly proportional to the number of living cells. The results were expressed as percentage survival with respect to untreated cells (control cells) using the formula below:

$$\text{Pourcentage viability (\%)} = \frac{A - B}{C - B} * 100$$

where A is the OD at 570 nm of the sample (cells treated with the fractions); B is the OD at 570 nm of the culture medium; C is the OD at 570 nm of the negative control (cells in culture medium without treatment) corresponding to 100% viability.

Figure 6:
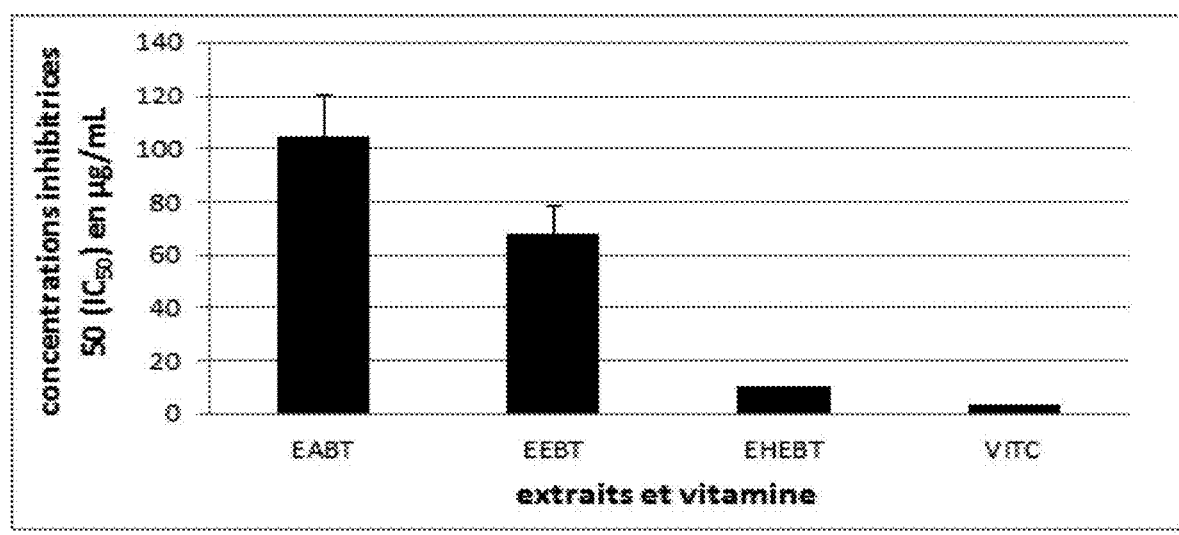
FIG. 6 shows representation of values of inhibitory concentration 50 of DPPH. radical by aqueous, ethanolic and hydroethanolic extracts of *B. toxisperma* and vitamin C in accordance with one embodiment of the present disclosure.

I.4.4.3. Determination Cellular Antioxidant Activity of Rough Extracts of *B. toxisperma* Fractions on SK-N-SH Cells Treated with Hydrogen Peroxide Principle:

The measure of the antioxidant capacity of living cells is possible through the use of a fluorescent borer such as 2',7' dichlorodihydrofluorescine di-acetate (DCFH-DA) which is capable of crossing the plasma membrane. When DCFH-DA enters the cell, it is deacetylated by membrane esterases and DCFH is transformed by intracellular reactive oxygen species into a fluorescent compound (DCF) which has an excitation wavelength of 488 nm and an emission wavelength of 530 nm.

Protocol:

SK-N-SH cells were inseminated in microplates of 96 wells (20 000 cells/well) and incubated for 48 hours in 200 µL of supplemented culture medium before the test. Firstly, the oxidative stress generating molecule ($H_2O_2$) was tested alone at a concentration of 50 M for 60 minutes. Secondly, tests were conducted involving pre-incubation for 60 minutes with fractions of *B. toxisperma* at concentrations of 1, 2.5 and 5 µg/mL. $H_2O_2$ was later added to make up a final concentration of 50 M and the setup incubated for 60 minutes. After treatment, the wells were rinsed with PBS, the old culture medium aspired and 500 µL of the fresh medium added; followed by 2',7'-Dichlorofluorescein diacetate (DCFH-DA, Sigma) to makeup a final concentration of 5 µM. The cells were incubated for an hour after which the medium was removed, the cells washed with PBS and trypsinated. After centrifugation, the solid phase containing cells was dissolved in 500 µL of PBS and 200 µL of the resulting suspension were transferred into the wells of another microplate. The microplate was deposited into a guava Eastcyte cytometer.

Data were analyzed using the Cytosoft 5.3 (Guava Technologies Inc.) software, and expressed as percentages of marked cells compared to the untreated control cells.

II. Results and Discussion

II.1. Results

II.1.1. Yields of Extraction and Contents of Bioactive Compounds

Table 4 below shows the yields from the extractions done on the bark of *B. toxisperma*, using different solvents.

TABLE 4

Yeilds from the different extractions on *B. toxisperma*

| Type of solvent | AEBT | EEBT | HEEBT |
|---|---|---|---|
| Yeild (%) | 16.3 | 19.0 | 22.5 |

AEBT: Aqueous Extract of *Baillonella toxisperma;*
EEBT: Ethanolic Extract of *Baillonella toxisperma*
HEEBT: Hydroethanolic Extract of *Baillonella toxisperma.*

The above values show that the highest yields were obtained with the solvent Water/Ethanol (50/50: v/v) which was called the HEEBT, followed by the ethanolic extract (EEBT), while the least yield was with water (AEBT).

The content of phenolic compounds is shown in table 5 below.

TABLE 5

Contents of total phenols, Flavonoids and Proanthocyans in the extracts of *B. toxisperma*

| Bioactive compounds | AEBT | EEBT | HEEBT |
|---|---|---|---|
| Phénols totaux (mg EAG/g MS) | 38.177 ± 2.218 | 41.545 ± 1.911 | 65.999 ± 4.142 |
| Flavonoïdes (mg EQ/g MS) | 4.094 ± 0.195 | 5.684 ± 0.364 | 4.666 ± 0.078 |
| Proanthocyanes (mg EAC/g MS) | 36.489 ± 7.281 | 41.847 ± 2.853 | 75.492 ± 2.630 |

EGA: Equivalent gallic acid; EQ: Equivalent quercetine; ECA: Equivalent cyanidic acid; DM: Dry matter.

We see that HEEBT has higher amounts of total phenols and proanthocyanes than EEBT, but the amount of flavonoids was greater in EEBT than in HEEBT.

II.1.2. The In Vitro Antioxidant Capacity of Aqueous, Ethanolic and Hydroethanolic Extracts of *B. toxisperma.*

II.1.2.1. Total Antioxidant Capacity

FIG. 3 shows the total antioxydant capacity of extracts of *B. toxisperma*. We observed that all extracts had antioxidant activity and HEEBT had the highest (38.879±5.697 mg EAA/g DM), while EEBT and AEBT had antioxidant activities of 32.002±5.697 mg EAA/g DM and 14.655±1.555 mg EAA/g DM respectively. Thus the classification is as follows: HEEBT>EEBT>AEBT.

II.1.2.2. Inhibitory Effects of Extracts on DPPH. Radical

FIG. 4 shows the inhibitory effects of HEEBT on DPPH. radical as well as that of vitamin C; while FIG. 5 shows those of EEBT and AEBT.

All extracts of *B. toxisperma* portrayed anti-radical activity which improved with increasing concentrations of extracts; with HEEBT attaining its maxima (83% inhibition) at a concentration of 30 µg/mL and AEBT and EEBT attaining theirs (78% and 75% inhibition) at 600 and 1000 µg/mL respectively. Vitamin C which served as reference already showed a 54% inhibition at a concentration of 5 µg/mL.

The inhibitory capacities of the different extracts were compared with that of vitamin C by calculating the inhibitory concentration 50 ($IC_{50}$) and the values represented in FIG. 6. HEEBT had the lowest $IC_{50}$ (10.025 µg/mL) followed by EEBT (68.04 µg/mL) while AEBT had the highest value (104.63 µg/mL). The classification of this activity can be summarized as follows: Vitamin C>EHEBT>EEBT> EABT.

II.1.2.3. Inhibitory Effects of Extracts on .OH Radical

Figure 7:
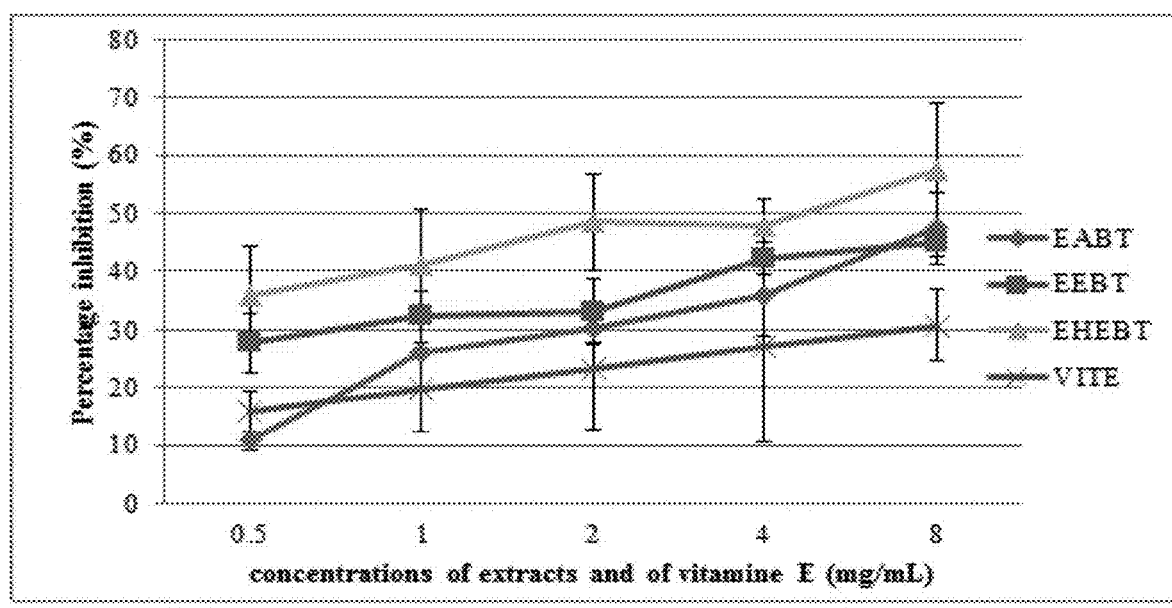
FIG. 7 shows variations curve of percentage inhibition of .OH radical with respect to concentrations aqueous, ethanolic and hydroethanolic extracts of *B. toxisperma* and standard vitamin E in accordance with one embodiment of the present disclosure.

The scavenging activity of the extracts on the .OH radical was evaluated by calculating the percentage inhibition of the oxidation of deoxyribose by .OH generated from the Fenton reaction. The results are presented in FIG. 7.

We observed a proportionate increase in the percentage inhibition with increasing concentrations of extracts. Trends in this activity are different for different extracts. At a concentration of 0.5 mg/mL, the aqueous extract showed an inhibition of 10.79%, the ethanolic extract showed 27.79% and the hydroethanolic extract, 35.83% inhibition.

Figure 8:
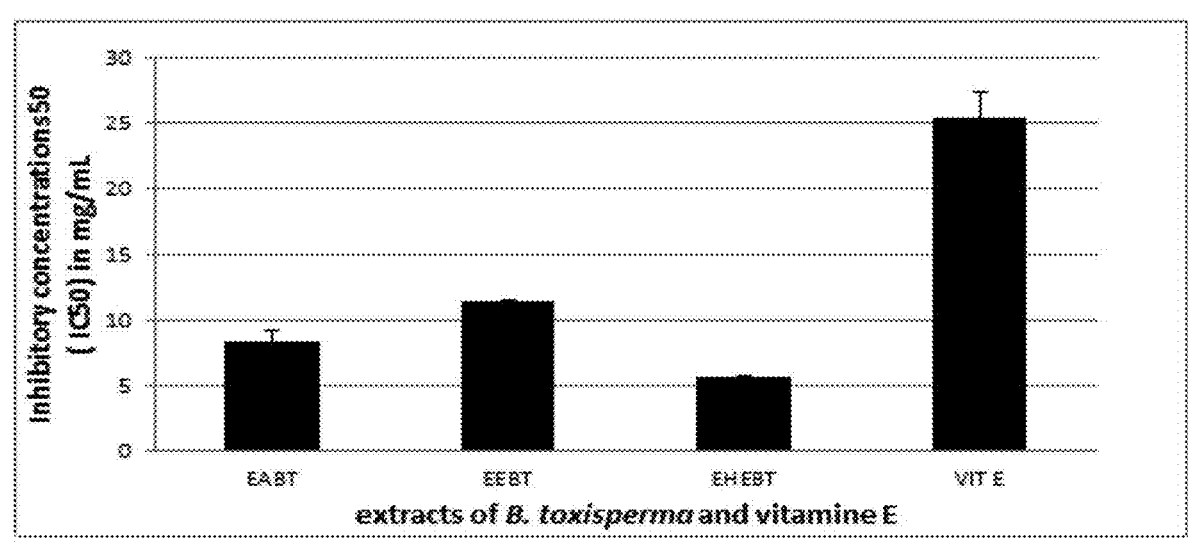

Values of inhibitory concentration 50 were determined in order to comparing the oxidation inhibition strength of deoxyribose. The values represented in FIG. 8 show that the hydrethanolic extract exhibited the best .OH scavenging activity, having an $IC_{50}$ of 5.625 mg/mL while the aqueous extract had $IC_{50}$=8.409 mg/mL and the ethanolic extract had $IC_{50}$=11.36 mg/mL.

All extracts portrayed a higher activated than that of vitamin E, which had an $IC_{50}$ of 25.3 mg/mL. Classifying the .OH radical scavenging activity gives the following trends: HEEBT>AEBT>EEBT>Vitamin E.

II.1.2.4. Inhibitory Effects on Lipid Peroxidation Induced in Brain Homogenates

Figure 9:
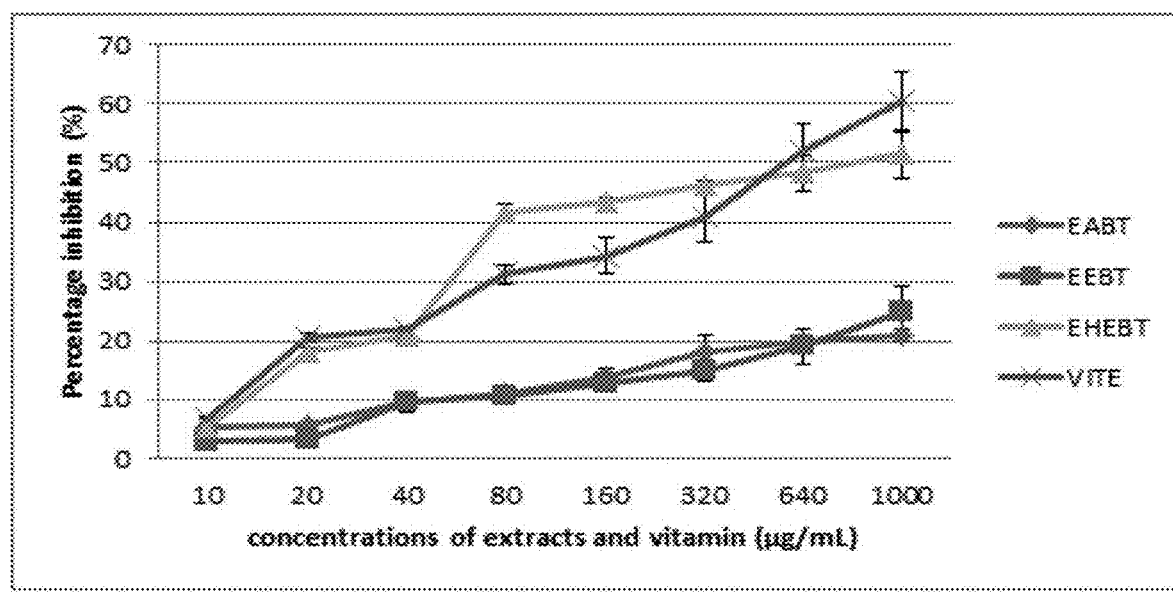
FIG. 9 shows variation curves of percentage inhibition of lipid peroxidation in brain homogenates for different concentrations of aqueous, ethanolic and hydroethanolic extracts of *B. toxisperma* and of standard vitamin E.

FIG. 9 shows the trends in the above mentioned effects. We saw that the inhibitory effects increases with increase in extract concentration. The most efficient inhibitions for both the extracts and vitamin E were observed at the concentration of 1000 µg/mL. At this concentration, we observed percentage inhibitions of 21.052, 25.011, 51.512 and 60.427 for aqueous extract, ethanolic extract, hydroethanolic extract and vitamin E respectively.

Figure 10:
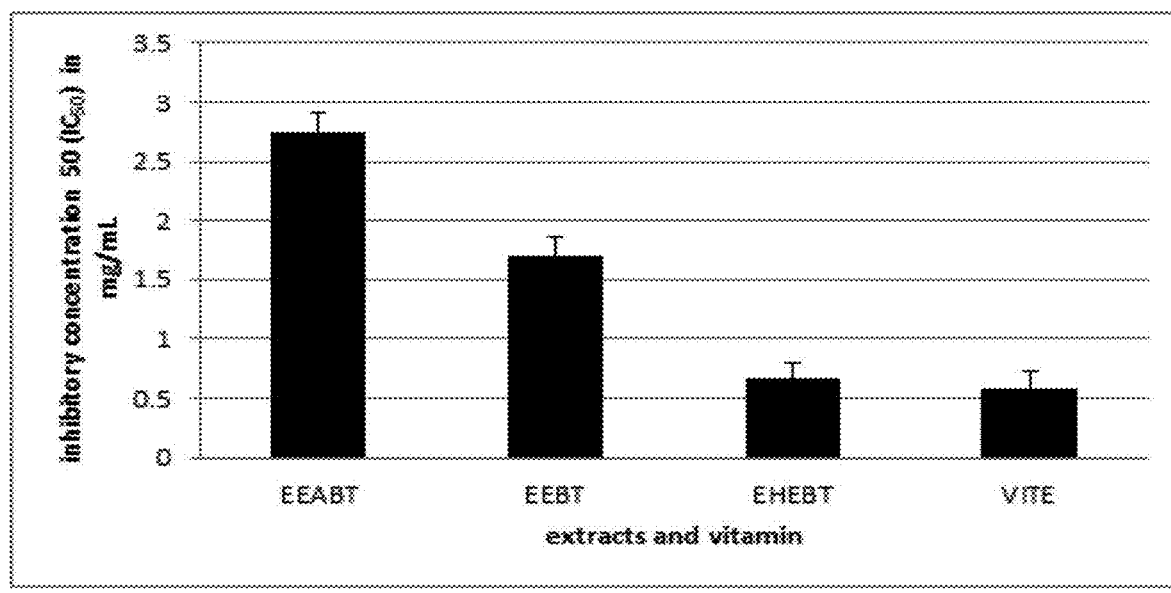
FIG. 10 shows values of inhibitory concentration 50 for aqueous, ethanolic and hydroethanolic extracts of *B. toxisperma* and standard vitamin E for the inhibition of lipid peroxidation induced in brain homogenates in accordance with one embodiment of the present disclosure.

The inhibitory concentrations is represented in FIG. 10. We observe that the hydroethanolic extract of *B. toxisperma* has an $IC_{50}$=0.664 mg/mL for lipid peroxidation induced in the brain, which is greater than those of the aqueous ($IC_{50}$=2.737 mg/mL), and the ethanolic extracts ($IC_{50}$=1, 692 mg/mL); and sensibly equal to that of vitamin E. ($IC_{50}$=0.574 mg/mL). Classifying the inhibition activities gives the following trends: Vitamin E>HEEBT>EEBT> AEBT.

II.1.3. Effects of Hydroethanolic Extract of *B. toxisperma* on Markers of Oxidative Stress Markers of Hepatic and Renal Toxicity after Administration of a Single Dose of Aluminum Chloride in Rats II.1.3.1. Effects of Hydroethanolic Extract on the Concentrations of MDA Table 6 shows the effects of administering aluminum followed by extracts, 24 hours later; on the MDA levels in the brain.

TABLE 6

Effects of hydroethanolic extracts of *B. toxisperma* on the concentrations of MDA in the brain of rats after administration of a single dose of aluminum chloride

| Groups | MDA (µM) |
|---|---|
| NC | 3.971 ± 0.406 |
| PC | 7.322 ± 0.784* |
| $BT_{150}$ | 4.437 ± 0.515# |

TABLE 6-continued

Effects of hydroethanolic extracts of *B. toxisperma* on the concentrations of MDA in the brain of rats after administration of a single dose of aluminum chloride

| Groups | MDA (µM) |
|---|---|
| $BT_{300}$ | 4.580 ± 0.554# |
| $VE_{100}$ | 4.631 ± 0.652# |

The PC group was compared with the NC group (p<0.05); all the treated groups were compared to the CP group (p<0.05) and all groups treated with extracts were compared with group that was treated with vitamin E (p<0.05).

We observe that Al induces a significant (p<0.05) increase in the level of MDA with respect to the negative control (NC). Treatment with HEEBT (150 and 300 mg/kg BW), as well as vitamin E, significantly (p<0.05) reduced the MDA level in rats as compared with the positive control (PC). Extracts and vitamin E portrayed equal activities.

II.1.3.2. Effects of Hydroethanolic Extract of *B. toxisperma* on Markers of Enzymatic and Non-Enzymatic Antioxidant System Catalase activity and the concentration of thiol proteins in the brain of rats after administration of aluminum and HEEBT are represented in table 7.

TABLE 7

Effects of hydrethanolic extracts of *B. toxisperma* on catalase activity and on the concentrations of thiol proteins in the brain of rats after administration of single dose of aluminum chloride

| Groups | Catalase (mM $H_2O_2$/min/mg of proteins) | Thiols proteins (µg/mg of proteins) |
|---|---|---|
| NC | 0.020 ± 0.004 | 0.317 ± 0.0732 |
| PC | 0.096 ± 0.008* | 0.313 ± 0.035 |
| $BT_{150}$ | 0.045 ± 0.010# | 0.359 ± 0.151 |
| $BT_{300}$ | 0.054 ± 0.010# | 0.443 ± 0.120 |
| $VE_{100}$ | 0.030 ± 0.003# | 0.299 ± 0.071 |

The PC group was compared with the NC group (p<0.05); all treated groups were compared with the PC group (p<0.05) and all groups treated with extracts were compared with groups that received vitamin E (p<0.05).

The table shows that Al provoked a significant (p<0.05) increase in the activity of catalase as compared with the negative control group (NC). Treatment of animals with HEEBT (150 and 300 mg/kg BW) and vitamin E tend to significantly (p<0.05) restore the activity of this enzyme to its normal level unlike the PC group. There was no significant difference in thiol protein contents between PC and NC groups. Only the group that was treated with the extract at a dose of 300 mg/kg BW portrayed a high level of thiol proteins with respect to the other groups.

II.1.3.3. Effects of Hydroethanolic Extract of *B. toxisperma* on Markers of Hepatic and Renal Toxicity.

Markers of hepatic toxicity (ASAT and ALAT) and renal toxicity (creatinine), evaluated after administration of a single dose of aluminum are represented in tables 8 and 9 respectively.

TABLE 8

Effects of hydroethanolic extract of *B. toxisperma* on the activity of plasma transaminases after administration of a single dose of aluminum chloride.

| Groups | ASAT (unité d'ASAT/mL) | ALAT (unité d'ALAT/mL) |
|---|---|---|
| NC | 72.828 ± 9.097 | 55.675 ± 6.115 |
| PC | 94.060 ± 11.735* | 76.846 ± 6.297* |
| $BT_{150}$ | 78.712 ± 13.072# | 56.283 ± 4.315# |
| $BT_{300}$ | 79.621 ± 14.870# | 52.432 ± 2.267# |
| $VE_{100}$ | 76.363 ± 1.868# | 60.135 ± 7.453# |

The PC group was compared with the NC group ($p<0.05$); all treated groups were compared with the PC group ($p<0.05$) and all groups treated with extracts were compared with groups that received vitamin E ($p<0.05$).

TABLE 9

Effects of hydroethanolic extract of *B. toxisperma* on the plasma concentration of creatinine in rats after administration of a single dose of aluminum chloride

| Groupes | Créatinine (mg/dL) |
|---|---|
| CN | 2.448 ± 0.190 |
| CP | 3.922 ± 0.494 |
| $BT_{150}$ | 2.530 ± 0.297 |
| $BT_{300}$ | 2.278 ± 0.011 |
| $VE_{100}$ | 2.297 ± 0.181 |

The PC group was compared with the NC group ($p<0.05$); all treated groups were compared with the PC group ($p<0.05$) and all groups treated with extracts were compared with groups that received vitamin E ($p<0.05$).

We observed that this toxin provoked a significant ($p<0.05$) increase in the activities of plasma transaminases as well as an insignificant increase in plasma creatinine concentrations, when compared with the NC group. On the other hand, treatment with HEEBT (150 and 300 mg/kg BW) and vitamin E after administering aluminum attenuated the effects provoked by the toxin and tend to normalize the activities of transaminases and plasma creatinine.

II.1.4. Antioxidant Effects of the Rough Methanolic Extract and Flavonoid Fractions of *B. toxisperma*

II.1.4.1. Flavonoides Content

Figure 11:
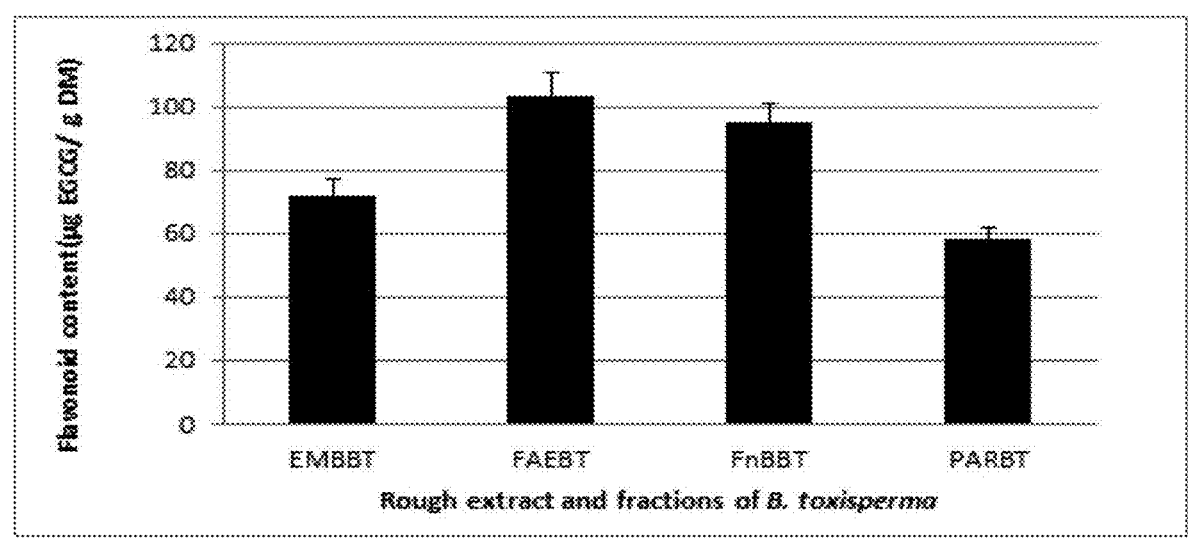

Fractionation of Flavonoids from the bark of *B. toxisperma* by use of organic solvents yielded 3 fractions: an ethyl acetate fraction made up of mono-glycoside flavonoids, an n-butanol fraction made up of di and tri-glycosides and a residual phase made up of highly polar flavonoids. FIG. 11 shows the flavonoid content in the rough extract as well as those in the fractions.

We noticed that the acetyl acetate fraction had the highest flavonoid content, followed by the n-butanol, the rough methanolic extract and then by the residual aqueous phase in that order.

II.1.4.2. Inhibitory Effects on DPPH. Radical

Figure 12:
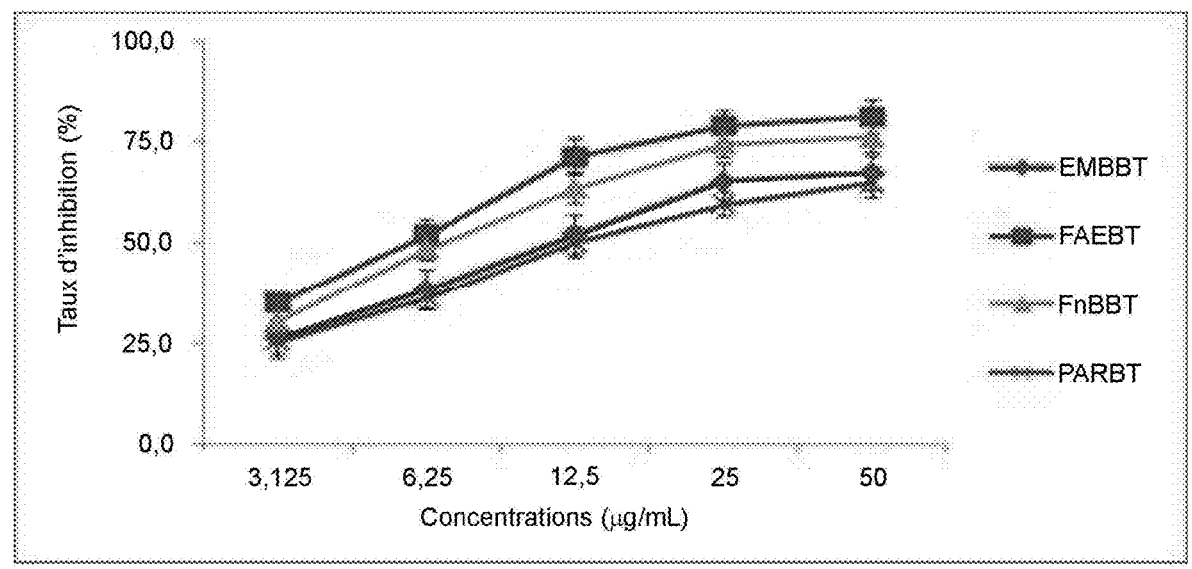
FIG. 12 shows variation curves of percentage inhibition of DPPH. radical for different concentrations of the rough methanolic extract and flavonoid fractions of *B. toxisperma* in accordance with one embodiment of the present disclosure.

The in vitro antiradical potential of the rough extract and flavonoid fractions was studied using the DPPH. method and results obtained are shown in FIG. 12. We observed that the DPPH. antiradical activity was proportional to the concentration of Flavonoids.

Figure 13:
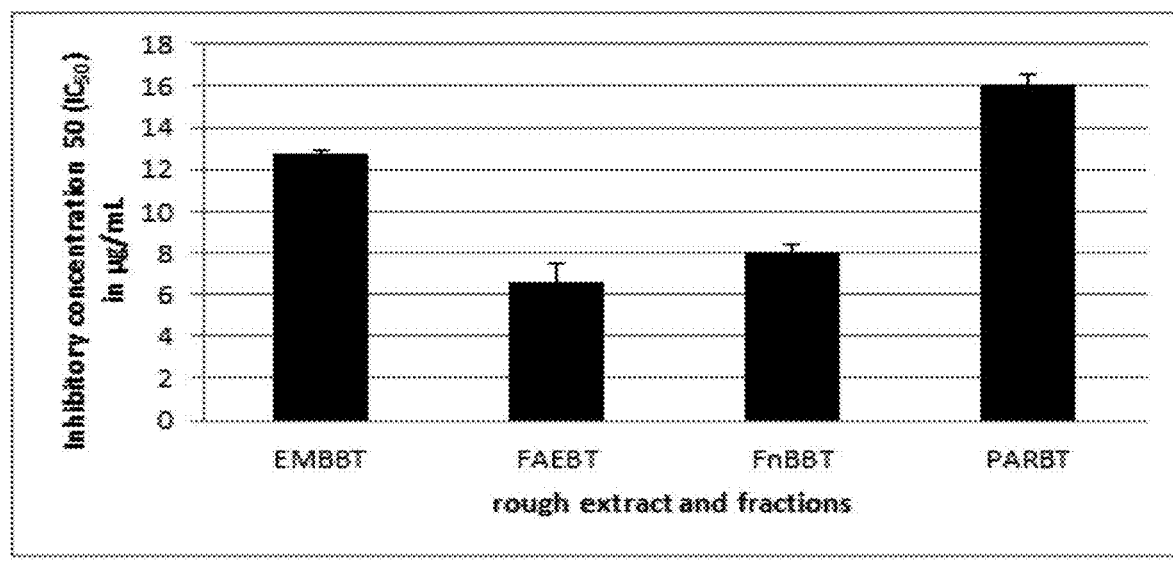
FIG. 13 shows representation of values for inhibitory concentration 50 of DPPH. radical for rough methanolic extract brut and fractions of *B. toxisperma* in accordance with one embodiment of the present disclosure.
Figure 14:
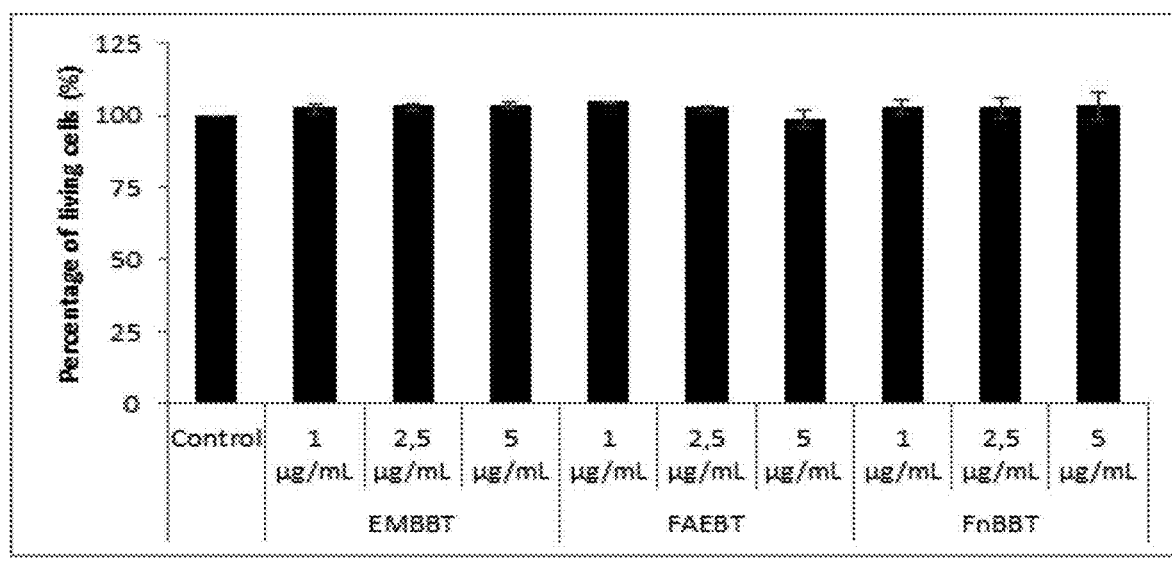
FIG. 14 shows effects of the rough extract and the fractions on the viability of SK-N-SH cells through the MTT test in accordance with one embodiment of the present disclosure.

The efficiencies of different samples to scavenge the DPPH. radical were compared by calculating the inhibitory concentration 50 for each of them. The results obtained are represented in FIG. 13. We observed that the efficiency of the acetyl acetate fraction (FAEBT) was highest ($IC_{50}$= 6.586 μg/mL) followed by the n-butanol fraction (FnBBT) ($IC_{50}$=8.025 μg/mL), the rough methanolic fraction (EMBT) ($IC_{50}$=12.795 μg/mL) and then the residual aqueous phase (PARBT) ($IC_{50}$=16.085 μg/mL) in that order. These results show that all our fractions exhibit DPPH. radical scavenging potentials and the trends in efficiency are as follows: FAEBT>FnBBT>EMBT>PARBT II.1.4.3. Effects of the Rough Extract and the Fractions on the Viability of SK-N-SH Cells FIG. 14 represents the mean viability (%) of SK-N-SH cells when placed in contact with either rough extracts of *B. toxisperma* or its fractions. We observed that after incubation in the different extracts at concentrations of 1, 2.5 and 5 μg/mL respectively, all tested samples did not affect the cells that were subjected to the MTT test as confirmed by the control.

Figure 15:
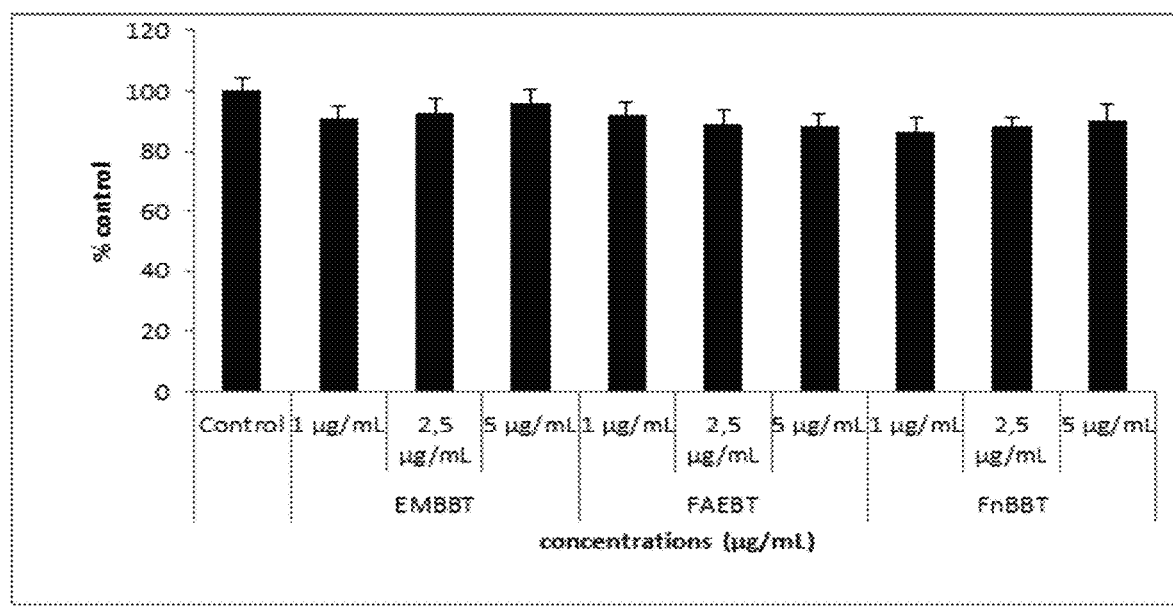
FIG. 15 shows effects of rough methanolic extract and flavonoid fractions of *B. toxisperma* on the production of ROS in SK-N-SH cell cultures in the absence of hydrogen peroxide in accordance with one embodiment of the present disclosure. * $P<0.01$ and ** $P<0.001$ significant difference as compared to the positive control ($H_2O_2$). For each fraction, values which do not have the same letter differ significantly ($p<0.05$).
Figure 16:
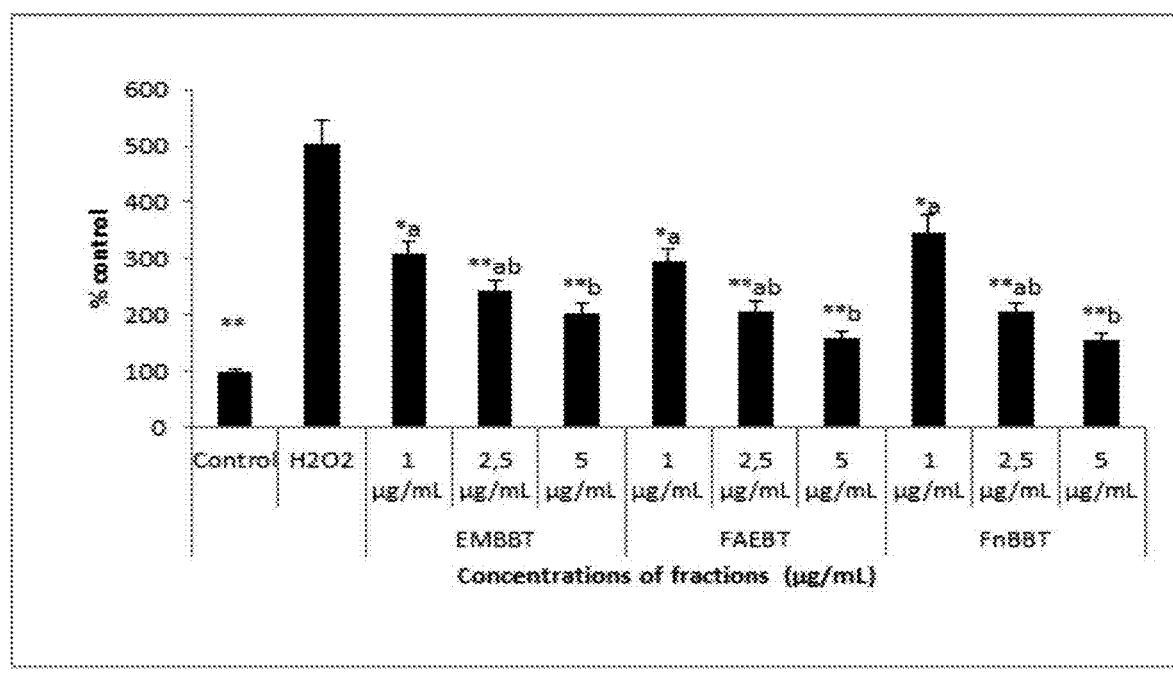
FIG. 16 shows effects of rough methanolic extract and flavonoid fractions of *B. toxisperma* on the production of ROS in SK-N-SH cell cultures in the presence of hydrogen peroxide in accordance with one embodiment of the present disclosure. * $P<0.01$ and ** $P<0.001$ significant difference as compared to the positive control ($H_2O_2$). For each fraction, values which do not have the same letter differ significantly ($p<0.05$).

II.1.4.4. Effects of Extracts on the Production Reactive Oxygen Species Induced by Hydrogen Peroxide in SK-N-SH Cell Cultures The antioxidant effects of the flavonoid fractions of *B. toxisperma* on intracellular reactive oxygen species (ROS) was studied using DCFH-DA fluorescence. The results obtained are represented in FIG. 15 and FIG. 16 below.

We observed that when incubated separately, the extracts did not modify the production of ROS in SK-N-SH cell cultures as compared with the control (normal neuron culture). On the other hand, when cells were incubated in the presence of 50 μM $H_2O_2$ (FIG. 16), modifications were observed.

A significant ($p<0.0001$) increase in the production of intracellular ROS was provoked upon incubation with 50 μM $H_2O_2$ when compared with the control; but pre-incubation in flavonoid fractions before induction of oxidative stress significantly brought the situation under control by reducing ROS production as compared with the positive control ($H_2O_2$). The observed effects were proportional to the concentration of extract used.

Control. Normal neuron culture+50 μM $H_2O_2$
EMBBT=Normal neuron culture+50 μM $H_2O_2$+different concentrations of rough methanolic extract of *B. toxisperma*
FAEBT=Normal neuron culture+50 μM $H_2O_2$+different concentrations of acetyl acetate fraction of *B. toxisperma*
FnBBT=Normal neuron culture+50 μM $H_2O_2$+different concentrations of n-butanol fraction of *B. toxisperma*

II.2. Discussion

II.2.1. Evaluation of the In Vitro Antioxidant Activity Extracts from *B. toxisperma*

Phenolic compounds from plants are always mixtures of different classes of polyphenols, which are selectively soluble in different solvents. The used of a mixture of water and alcohol has the added advantage of modulating the polarity of alcoholic solvents and thereby facilitating the extraction of some plants as proposed by Zohra and Fawzia (2011). This could explain why the hydro-ethanolic extract had the best extraction yield and contained the highest amount of polyphenols. Many methods have been developed to study the in vitro activity of natural extracts. According to Prior et al. (2005) the antioxidants that inhibit the production of free radicals during experimental exercises could act either by transferring a hydrogen atom or an electron in order to reduce oxidized species.

In methods which are based on the transfer of hydrogen atom, we evaluated the global capacity of an antioxidant to arrest free radicals by donating an atom of hydrogen; while in methods which are based on the transfer of an electron, we evaluate the capacity of an antioxidant to donate an electron which could reduce any oxidized species. Given the different physicochemical factors involved, Prior et al. (2005) recommended the use of more than one type of test in order to confirm antioxidant activity.

The results showed that all the extracts had good total antioxidant capacities, good antiradical activities and good ability to inhibit lipid peroxidation in vitro as compared with vitamins C and E. This in vitro antioxidant activity could be explained by the fact that most of the phenolic antioxidants contained in the extracts poses free hydroxyl-phenyl groups and conjugated double bonds in their structure, which according to Bartosz (2003), are capable of supplying a hydrogen atom or an electron to a free radical or a metal. It is for this reason that Ghasemzadeh et al. (2010) associated the antioxidant activity of an extract to its polyphenol content. This should explain why the hydro-ethanolic extract had the best antioxidant activity in vitro.

II.2.2. Evaluation of Neuro-Protective Activity of the Hydroethanolic Extract of B. toxisperma After identifying the hydro-ethanolic extract of B. toxisperma as that with the best antioxidant activity, we proceeded to study its protective effects against aluminum chloride-induced neurotoxicity. The animal experimental model used is one which Nade and Yadav (2010) as well as Sadhana et al. (2011) declared as being the most currently used to study neuroprotective properties of plants which could be used in the management of Alzheimer's disease. Aluminum was used as the neurotoxin in this case, to simulate a situation where nerve cell-damage is associated to the production of free radicals and other forms of oxidative stress. It is for this reason that we evaluated markers of oxidative stress, liver toxicity and renal toxicity in rats.

Data collected 4 days after administering a unique dose of aluminum chloride to rats, showed a significant increase in MDA levels which translate an evident increase in lipid peroxidation. Similar results were obtained by Sadhana et al (2011) who showed that Al induces significant increase in MDA levels in the brain and liver four days after an intra-peritonial administration of a unique dose of 32.5 mg/kg BW of aluminum nitrate in Sprague Dawley rats. The production of MDA suggests the implication of cell damages induced by free radicals according to Newairy et al. (2009), would have been induced by aluminum toxicity. The administration of plant extract at doses of 150 and 300 mg/kg BW 24 hours after administration of Al, significantly reduced MDA production as compared to the positive control group. These results suggest that hydro-ethanolic extract of B. toxisperma would protect the brain of rats from lipid peroxidation. This protective effect would be due to the presence of phenolic compounds in the plant extract, which demonstrated a good anti-radical activity in vitro.

Superoxide dismutase and catalase are important antioxidant enzymes which protect the brain from nerve damage initiated by peroxydases. According to Jones et al. (1981), the fact that the Michaelis-Menten constant (Km) of catalase is greater than that for Glutathion peroxydase (GPx), implies that catalase would decompose $H_2O_2$ more efficiently at high concentrations. This should explain why in the course of this study, we did not observe significant variations in the concentrations of glutathione thiol protein (which is a substrate of GPx) but rather a significant increase in catalase activity which would probably have been due to a high production of $H_2O_2$ induced by Aluminum. Davies et al. (1979) had proven that the concentration of $H_2O_2$ influences the activity of catalase; therefore we could directly associate the modifications in catalase activity to variations in $H_2O_2$ concentration, since the latter is its only substrate. In this study, the significant increase in the activity of this enzyme in the positive control group (not treated with extract) would certainly be due to brain cells' response to oxidative stress induced by AL; and the restoration to normal activity in treated groups would be due to decrease in the concentration $H_2O_2$ or that of other ROS which could have been trapped by the plant extracts. Newairy et al. (2009) and Nade and Yadav (2010) found out that during sub-acute or chronic exposition of rats to Al, there is a significant decrease in the activity of catalase; this could reinforce the hypothesis that the hydro-ethanolic extract of B. toxisperma protects the brain from oxidative stress induced by Al.

Results further showed that Al induced an increase in plasma creatinine level in untreated groups, which is in accordance with earlier findings by Sadhana et al (2011). Animals treated with plant extracts recorded lower levels of creatinine than those of the untreated group. Given that creatinine is a marker of renal toxicity, we can suggest that the hydro-ethanolic extract of B. toxisperma could protect renal cells from aluminum induced toxicity.

II.2.2. Evaluation of the Antioxidant Activity of Rough Methanolic Extract and Fractions of B. toxisperma According to Pietta (2000) flavonoids are the major antioxidants in plants, whose presence would account for most of the health benefits derived from plants. It is for this reason that we first got the rough methanolic extract, and then proceeded with fractionation to obtain flavonoid fractions. The in vitro tests revealed that the rough methanolic extract's ability to inhibit the DPPH. radicals is lower than that for the flavonoid fractions. Rice-Evans et al. (1996) found out that the methylation and glycation of flavonoids reduces the number of free hydroxyl groups in their structure, thereby reducing their activity. It should be for this reason that the acetyl acetate fraction (having less glycation) was more active than the n-butanol fraction (which has more glycation).

The cellular antioxidant activity of SK-N-SH cells of human linage was studied in the presence of the rough extract and the flavonoid fractions of B. toxisperma. According to Ba et al. (2003), SK-N-SH neuroblastomas of human linage respond to the study of a number of nerve disorders including β-amyloid peptides and mitochondrial permeability making them suitable for the proper estimation of neurotoxicity and nerve protection. After demonstrating that most flavonoids can inhibit the proliferation of diverse lineages of cancer cells without being toxic to man, Benavente-Garcia and Castillo (2008) proposed the use of flavonols (such as quercetin) as chemo-protective agents since they are capable of inhibiting angiogenesis and tumor proliferation in vitro. In the course of our study, we studied the cytotoxicity using 3 concentrations of rough extract and flavonoid fractions by the MTT test. Results showed that at these concentrations, the viability of the cells is not affected.

Peroxides are continuously produced by cells that consume oxygen. Of these peroxides, $H_2O_2$ is the peroxide that is produced in the greatest quantity as stated by Dringen et al. (2005). According to Heo et al. (2008), the fact that $H_2O_2$ provokes the rapid formation of ROS, which can lead to cell apoptosis, makes it a good inducer of oxidative stress during in vitro experimentation. Results from our study showed that the exposal of SK-N-SH cells to $H_2O_2$ induces an intracellular production of reactive oxygenated species (ROS). These findings are similar to those of several authors: Chang-O et al. (2011) showed that the exposal of PC 12 cells to $H_2O_2$ induces massive production of ROS; while Wang et al. (2008) showed that $H_2O_2$ induces increased the production of ROS human SK-N-SH neuroblastoma. Pre-incubation in the rough methanolic extract and flavonoid fractions significantly reduced the production of ROS. This antioxidant activity could be assimilated to the fact that the extract and its fractions contain compounds like epigallocatechin-3-gallate (EGCG) or quercetin. According to Schroeder et al. (2008) EGCG accumulates in the mitochondria where it acts as a local scavenger of free radicals thereby protecting neurons; and Kshitija et al. (2012) also found that quercetin protects MR32 neuroblastoma of human lineage from $H_2O_2$-induced oxidative stress, by increasing the activity of antioxidant enzymes.

Though the evaluation of antioxidant activity by the DPPH. method showed a marked difference between the activities of the rough extract and its flavonoid fractions, their cellular antioxidant activity did not really differ. This result suggests that fractionation might not significantly increase the antioxidant activity of B. toxisperma. To some extent, we could postulate that flavonoids are not probably the major compounds that are responsible for the antioxidant and nerve protective activities of B. toxisperma. If this is the case then other phenolic compounds could be involved.

Among other things, the present disclosure discloses the antioxidant and neuro-protective activities of the extracts and the flavonoid fractions of B. toxisperma. Specifically, the present disclosure reduces free radicals in a mammal and protects neurons in a mammal from oxidative stress by using extracts of B. toxisperma.

Several methods were used to evaluate the antioxidant potential, while two experimental models (stem cell culture model and animal model) were used to study the neurotoxicity aspect. The evaluations of the amount of bioactive compounds and of the antioxidant potential revealed that the aqueous, ethanolic and hydro-ethanolic extracts of B. toxisperma are rich in bioactive compounds (polyphenols, flavonoids and proanthocyans); that they have reducing and antiradical activities as well as the ability to inhibit lipid peroxidation. The choice of hydro-ethanolic extract for the next phase of study was based on the fact that it had the highest polyphenol and proanthocyan contents; in addition, it also portrayed the most efficient antioxidant activity in vitro.

Studies done on animal models using the hydro-ethanolic extracts of B. toxisperma showed that this extract has neuro-protective effects which are similar to that of vitamin E. This is seen through its ability to reduce lipid peroxidation induced by aluminum toxicity and to reinforce the antioxidant defense system of the brains of Wistar rats.

Studying the antioxidant effects of the rough methanolic extracts and the flavonoid fractions of B. toxisperma in vitro revealed that the fractions had a greater antioxidant activity than the rough methanolic extract, but the antioxidant activity on SK-N-SH cell cultures portrayed similar results for both the rough methanolic extract and its fractions.

The present disclosure brings out the fact that extracts as well as flavonoid fractions gotten from the bark of B. toxisperma have antioxidative properties have various benefits, including but not limited to, acting as a powerful antioxidant, providing neuroprotective protection and protecting cells from oxidative stress. This plant could be a new source of medication to prevent oxidative damages on neurons, in an attempt to prevent Alzheimer's disease.

It should be understood, of course, that the foregoing relates to exemplary embodiments of the invention and that modifications may be made without departing from the spirit and scope of the invention as set forth in the following claims.

What is claimed is:

1. A method of treating Alzheimer's disease or Parkinson's disease in a human in need thereof comprising administering 150 mg-300 mg per day of an extract of Baillonella toxisperma to said human in need thereof to effectively treat the Alzheimer's disease or Parkinson's disease in the human in need thereof.

2. The method of claim 1, wherein the Baillonella toxisperma extract is a water extract.

3. The method of claim 1, wherein the Baillonella toxisperma extract is an ethanol extract.

4. The method of claim 1, wherein the Baillonella toxisperma extract is from the stem or the bark of Baillonella toxisperma.

5. The method of claim 1, wherein the Baillonella toxisperma extract is a hydroethanol extract.

6. The method of claim 1, wherein the Baillonella toxisperma extract is a dried powder.

7. A method of treating Alzheimer's disease in a human in need thereof comprising administering 150 mg-300 mg per day of an extract of Baillonella toxisperma to said human in need thereof to effectively treat the Alzheimer's disease in the human in need thereof.

8. The method of claim 7, wherein the extract of Baillonella toxisperma is a water extract of Baillonella toxisperma.

9. The method of claim 7, wherein the extract of Baillonella toxisperma is an ethanol extract of Baillonella toxisperma.

10. The method of claim 7, wherein the Baillonella toxisperma extract is from the stem or the bark of Baillonella toxisperma.

11. The method of claim 7, wherein the Baillonella toxisperma extract is a hydroethanol extract.

12. The method of claim 7, wherein the Baillonella toxisperma extract is a dried powder.

13. A method of treating Parkinson's disease in a human in need thereof comprising administering 150 mg-300 mg per day of an extract of Baillonella toxisperma to said human in need thereof to effectively treat the Parkinson's disease in the human in need thereof.

14. The method of claim 13, wherein the Baillonella toxisperma is administered as a water extract of Baillonella toxisperma.

15. The method of claim 13, wherein the Baillonella toxisperma administered is an ethanol extract of Baillonella toxisperma.

16. The method of claim 13, wherein the Baillonella toxisperma extract is from the stem or the bark of Baillonella toxisperma.

17. The method of claim 13, wherein the Baillonella toxisperma extract is a hydroethanol extract.

18. The method of claim 13, wherein the Baillonella toxisperma extract is a dried powder.

* * * * *